(12) United States Patent
Wayne et al.

(10) Patent No.: US 6,207,377 B1
(45) Date of Patent: Mar. 27, 2001

(54) **METHOD FOR CONSTRUCTION OF THERMUS-*E. COLI* SHUTTLE VECTORS AND IDENTIFICATION OF TWO THERMUS PLASMID REPLICATION ORIGINS**

(75) Inventors: Jay Wayne, Flushing, NY (US); Shuang-yong Xu, Lexington, MA (US)

(73) Assignee: New England Biolabs, Inc., Beverly, MA (US)

( * ) Notice: Subject to any disclaimer, the term of this patent is extended or adjusted under 35 U.S.C. 154(b) by 0 days.

(21) Appl. No.: 09/134,246

(22) Filed: Aug. 14, 1998

(51) Int. Cl.$^7$ .............................. C12Q 1/68; C12P 19/34; C12N 15/74; C12N 15/63; C12N 1/20
(52) U.S. Cl. .......................... 435/6; 435/91.1; 435/471; 435/320.1; 435/252.3; 536/23.1; 536/24.1
(58) Field of Search ..................... 435/6, 69.1, 252.31, 435/252.33, 320.1, 91.1, 471, 252.3; 536/23.1, 24.1

(56) References Cited

U.S. PATENT DOCUMENTS 5,786,174 * 7/1998 Weber et al. ..................... 435/69.1

OTHER PUBLICATIONS

Munster et al, Appl. Environ. Microbiol., 50:1325–1327 (1985).
Kristjansson et al., 'Thermophilic Bacteria', Kristjansson, ed., p. 1–18 (1992).
Hishinuma et al., J. Gen. Microbiol. 103:193–199 (1978).
Eberhard et al., Plasmid 6:1–6 (1981).
Vasquez et al., FEBS Lett. 158:339–342 (1983).
Kristjansson, Trends Biotech. 7:349–353 (1989).
Coolbear et al., Adv. Biochem. Eng. Biotech. 45:57–98 (1992).
Wiegel et al., CRC Crit. Rev. Biotech. 3:39–108 (1984).
Koyama et al., J. Bacteriol. 166:338–340 (1986).
Raven et al., Nucl. acids Res. 21:4397 (1993).
Oshima et al., J. Sys. Bacteriol. 24:102–112 (1974).
Wayne et al., Gene 195:321–328 (1997).
Sambrook et al, 'Molecular Cloning A Laboratory Manual', 2nd ed. (1989), pp. 17.29–17.33.
Hartmann et al., J. Bacteriol., 171:2933–2941 (1989).
Maseda et al., FEMS Microbiol. Lett. 128:127–134 (1985).
McMacken et al., DNA Replication (Chapter 39) p. 586–587 in *Escherichia coli* and *Salmonella typhimmarium*, Amer. Soc. for Microbiol., Washington DC (1987).
The Tsp45I restriction–modification system is plasmid-–borne within its thermophilic host. Wayne et al. Gene. vol. 202:83–88, Dec. 1997.*
Towards a unified grammatical model of sigma 70 and sigma 54 bacterial promoters. Collado–Vides, J. Biochimie vol. 78:251–363, Jun. 1996.*
DNA micorloops and microdomains: A general mechanism for transcription activation by torsional transmission. Travers et al. J. Mol. Biol. vol. 279:1027–1043, Aug. 1998.*

* cited by examiner

*Primary Examiner*—Robert A. Schwartzman
*Assistant Examiner*—William Sandals
(74) *Attorney, Agent, or Firm*—Gregory D. Williams

(57) ABSTRACT

The present invention relates to cloned DNA containing origin of DNA replication and to cloned DNA encoding repliation protein, RepT.

1 Claim, 13 Drawing Sheets

FIG. 1

```
                10                      30                      50
GTGAAGAACGAAAAAACCTTCTTTGAAGAGCTTTACGAGGCTTTAGAGGAAACCCACGAC
 M  K  N  E  K  T  F  F  E  E  L  Y  E  A  L  E  E  T  H  D
                70                      90                     110
AACACCGATGCCACTAGGGGGTCAGATAGGGGGTCAGAGGACTTCTTCTTGGCCACCGAC
 N  T  D  A  T  R  G  S  D  R  G  S  E  D  F  F  L  A  T  D
               130                     150                     170
CCCCCTCCAGATGGAGGTGCCGAAAATCGCCTCGCGAAGGGCTTTACATACCAAAAAGAG
 P  P  P  D  G  G  A  E  N  R  L  A  K  G  F  T  Y  Q  K  E
               190                     210                     230
GCACTTAGGATTGCTTTACCCGAGAAAGACCATGAGGCTTTCCTTTCCTCTGTTGGGGCC
 A  L  R  I  A  L  P  E  K  D  H  E  A  F  L  S  S  V  G  A
               250                     270                     290
CCCCCTATACCACCAGCTGAACCCCCCGTTGGGAATGTATGTCAAGCCGTCCAGGACGGG
 P  P  I  P  P  A  E  P  P  V  G  N  V  C  Q  A  V  Q  D  G
               310                     330                     350
CCTCAGAAGCTTCTGGAACTCCTCCAGGAGATTGCCCGCTCCACCATCCCCTACGGCAAC
 P  Q  K  L  L  E  L  L  Q  E  I  A  R  S  T  I  P  Y  G  N
               370                     390                     410
CGGGAGCTCTGGAGGAAGGTGGGGACGGTCGTCTTCATGGTCCCCCTGGAGATGTTGGCC
 R  E  L  W  R  K  V  G  T  V  V  F  M  V  P  L  E  M  L  A
               430                     450                     470
CTCAACCTGGGGGTCACCCGGCAGACCGTCCACGCCTGGAAGAAGGTCCTTGAGAAAAAG
 L  N  L  G  V  T  R  Q  T  V  H  A  W  K  K  V  L  E  K  K
               490                     510                     530
GGCCTGGTGGCCACCGACGTCCTTCACCAAACCGTCAACGGGGAGCGCCGGGCCATCGGC
 G  L  V  A  T  D  V  L  H  Q  T  V  N  G  E  R  R  A  I  G
               550                     570                     590
ACCCTTTGGGCCGTCCGGCTGAGGCCAGGGAAAGCCAGGCTCACCCTGGACGACTACATC
 T  L  W  A  V  R  L  R  P  G  K  A  R  L  T  L  D  D  Y  I
               610                     630                     650
TACCCCTGGAGGAACCTCGCCCTAGACATGGCCAACGGCGTGCTCTCCTTCAACTGGGTC
 Y  P  W  R  N  L  A  L  D  M  A  N  G  V  L  S  F  N  W  V
               670                     690                     710
AAGGCCTACCAGGACCACGGAATCCGCCCCACCCTGGACGTGCTGGTCCTCTGGGCTCAG
 K  A  Y  Q  D  H  G  I  R  P  T  L  D  V  L  V  L  W  A  Q
               730                     750                     770
GGGAAAAGGGTGATGCCCAACACCAAGACCGTGGCCGTTGACCTGGGCCTCATCCTGGTC
 G  K  R  V  M  P  N  T  K  T  V  A  V  D  L  G  L  I  L  V
               790                     810                     830
CTCCCCGAGGTGGAGCGTTCCAAACTCCCGGCCCTTATCACCCTCATTGCTACGTACATT
 L  P  E  V  E  R  S  K  L  P  A  L  I  T  L  I  A  T  Y  I
               850                     870                     890
GCCGATCTCCTAGATGACCGTCGTTCAAGACGTTTCTATGCAGGCTTGCTGTGGGCTGTG
 A  D  L  L  D  D  R  R  S  R  R  F  Y  A  G  L  L  W  A  V
               910                     930                     950
GCCAGGGGTGAACTCCCCGCGCAATATCTATTTGCCGTCCTAATGCGGGTTATCCGAGAT
 A  R  G  E  L  P  A  Q  Y  L  F  A  V  L  M  R  V  I  R  D
               970                     990                    1010
TACACGGATGGCCATCTGACACGACCGGGAGCGTACCTAGTGAAGACCCTCAAGGAGGCC
 Y  T  D  G  H  L  T  R  P  G  A  Y  L  V  K  T  L  K  E  A
TCCTGA
 S  *
```

FIG. 2

```
  1  CTATAACGGCCTTTTAGGAGGGGGGATTGCCAGCCGCTGGGCTGACGGTTATTTTGGACC

61  CATAAAAAGGCGAAACCGAGGCGGTTGCCCCGGATCACCCCCAAGACCTAGGGTAACGCC

121  TCGGGCTCCAGATGACAAGGAGGTCCGAGGGTGAAGAACGAAAAAACCTTCTTTGAAGAG
                               M  K  N  E  K  T  F  F...(RepT)
```

FIG. 3A

```
   1 tctagaaggt cagggtggac aaggaaaaca ccatagcccc tgccaagaag atggacgagt
  61 tggtgtccgg aaaagtggcc atccgggggcg ctcttgacaa ctattttcca gcggtggcca
 121 ccggcattgg ccacgaggta cgagcttgtg gagtagacgg ccacaaaggg gtcgtcctca
 181 aacttctttt ctagtgccgc ttggacgaag gggaggaaga ggaaaggctt catggcctca
 241 cctccttccc ctcctccttg gcggccttag cggcgtaaaa ctctgagacg gcctgaagtt
 301 tagggatttc gctttcgggg ataagaatcc ggcggctcag gggatgccgg atggcccta
 361 tcctgccgtc ccttatgtac tcgtaaatgg tggccttggg tactttaaac cgttctgaaa
 421 cttctctaac agagagcaca aaacctctaa aaacctatca atcccaccga ttccagtata
 481 ccataaatgg cacaaagttt tgagaaggtg gtcaaacaaa aaggctttct cggtcaggtt
 541 atggtgaggt ggggggcggtc aaaggccgac ttaagtttgg taaagccggg aggaagcaaa
 601 ccggggtgtt accatgcaac agatggccga gtggaacgtg tggacacaga gaagcgttga
 661 gcttctggag aaggggtatt tggataaact actgcaggtc tataaagggg aaagtggctc
 721 ttcgaggtca gtaccagagg aggtagagga aaaacttcgc gaggcctaca aggcatacga
 781 ggggaggcag gatagtccgg aggcagaaac gaaactcgtg gaagccgtgc taaatgccag
 841 aaaaaaggtc gagcggtccc ccttcaatca cccctacctg cctttggtct actacctggt
 901 ttcggaaaaa gcagaaaaag cgaacaaggc ccttgaggag gcattgcagg aggttgcctc
 961 aaagcaccca gaaaccatcc gcgtcctggc caaggaagcg caaagaagag gcgtagaagc
1021 cttgatccaa aggctcaagg agcctcccga aataaatcgg cagataggggc cgatgttcaa
1081 aaggtggtac aaagaagagc taaggggggaa aatagaagag aggcttccag gccctaccaa
1141 accaaagatt gtggtagtat ccctgaaaa aagtaaaccg gagcaagcac cccttattgc
1201 ggagagagaa gcgggcatca tcatatacac gggatcggat gaagctttga aagatgccgc
1261 caaggaaaac ctgggccttg gcgaggaagc agaactaggc accaagggcg tagatttcta
1321 cgtggtcatc cggcgtagcc ctgaagagac atggcaccta acaggagaag tgaagtttca
1381 atccgacttt ggcggaaacc aagacaacca gaaactagta gcaaaggctt ccataaggtt
1441 ggaccttgag aagaggcaca taggaatagt ggtggtggac ggaatgcctg tggtgagcaa
1501 gtttcgtggg tgggccggac tggggaaaga aacgatcgtt acatccgtac tcctccttcc
1561 agacctgata gcggagctct accaaaaggg tgaagaagcc ctgggcctct agaaggcgga
1621 cacaatctca aacttgtgct gtagcctggg gaaatcctct aacacccttc tagtgaaggc
1681 tttgaccgcc tcccaggagg catctatgcc gatggatcgc cgctttaaga gggtgaggc
1741 tataagcgta gtaccggagc ctgcgaaggg atcgagcact aaatcccccct cgttactccc
1801 tgtttggacg atgagcttga gcatgtccag attttttctcg gtggggtatc gcgggtacgg
1861 aggatccttg aactgccaaa cgtcctggag cttcttcccc ttcttcaggc gatcccgagc
1921 gtaaactttc ttccgcggca ccccgttctt tgaccagaca ataagcccct gagcgtctag
1981 ctcgtcaagc ttctccgggg gatagcgcca atgccgtcca ggaggggggaa gtattcctcg
2041 ccaaggcctt ccggtagggc catccttggt ttctccagga gcatgcaggg gattggtggt
2101 gtaccgttcc ccgttctcgt ctacaaaggg gaaaagccta gcgatctcct cttccgaata
2161 ggggctagcc gattcgttcc aaacgtagtc ccgcgttttg gagtagacga ggatcatgtc
2221 cttttgcgat ccgaaggcct tacgggaaaa gttttggga tttgaagcga tgcgggcgat
2281 atggttaacg aagtttcgcc ggccaaagac ctcatcaagg atgagcttca cctcgaaccc
2341 gtatttctcg tctatgtgaa cgaagatcag tcctgagtcc gccatcagct ccctgagaag
2401 tatcaagcgc tccctcagga actccacaaa ctgaggacca tcgagggtgt catcgtagcc
2461 caactgaccg ttttttgggct ggctgacggt agcaacgcga tctgtttcat cgccgccaac
2521 gagaaactgc tggccggttc cataaggcgg gtcaatatag accaactgga ccttccccgc
2581 atacccacca ggctcccgga gcatccaccg gagaacctga ccgttttccc ccaaaaagta
2641 ggtgccaata ggatcaatct caaaaaggggg ggcatttccc cctaggaaga ggagggtttc
2701 ttttcgcaaa acaagttgtg gggtgggctg atcaagaatc tccttctcat cgcgttttcc
2761 ggggtagacc aacctaaagg gcgaaggttc cgaggttttc gaggctttca aggggggcttt
2821 tcgggtcaaa ccagggtagc tacgctcat tcttccctcc ccacagcgct cttaagcagg
2881 acctcatcac ccacaaccct cacgcactcc aaccaaggaa tccgccaaag gcggcctacc
2941 ttttgagccc gtatcttccc ctgacgtata gaccttcgga tcgtctcagg gtgcacccga
3001 aggatgtctg caagctcctc gggggtcagg tacacgggct tcatcctcat gacacaacct
3061 tacccccacag aggacaacac atgcaactat gggcaaagta gacaacgaga ccaaaagctt
3121 gggccactct ctcaggaggc ctccttgagg gtcttcacta ggtacgctcc cggtcgtgtc
3181 agatggccat ccgtgtaatc tcggataacc cgcattagga cggcaaatag atattgcgcg
3241 gggagttcac ccctggccac agcccacagc aagcctgcat agaaacgtct tgaacgacgg
3301 tcatctagga gatcggcaat gtacgtagca atgagggtga taagggccgg gagtttggaa
```

FIG. 3B

```
3361 cgctccacct cggggaggac caggatgagg cccaggtcaa cggccacggt cttggtgttg
3421 ggcatcaccc ttttcccctg agcccagagg accagcacgt ccagggtggg gcggattccg
3481 tggtcctggt aggccttgac ccagttgaag gagagcacgc cgttggccat gtctagggcg
3541 aggttcctcc aggggtagat gtagtcgtcc agggtgagcc tggctttccc tggcctcagc
3601 cggacggccc aaagggtgcc gatggcccgg cgctccccgt tgacggtttg gtgaaggacg
3661 tcggtggcca ccaggccctt tttctcaagg accttcttcc aggcgtggac ggtctgccgg
3721 gtgaccccca ggttgagggc caacatctcc aggggggacca tgaagacgac cgtccccacc
3781 ttcctccaga gctcccggtt gccgtagggg atggtggagc gggcaatctc ctggaggagt
3841 tccagaagct tctgaggccc gtcctggacg gcttgacata cattcccaac gggggggttca
3901 gctggtggta tagggggggc cccaacagag gaaaggaaag cctcatggtc tttctcgggt
3961 aaagcaatcc taagtgcctc ttttggtat gtaaagccct tcgcgaggcg attttcggca
4021 cctccatctg gaggggggtc ggtggccaag aagaagtcct ctgacccct atctgacccc
4081 ctagtggcat cggtgttgtc gtgggtttcc tctaaagcct cgtaaagctc ttcaaagaag
4141 gttttttcgt tcttcaccct cggacctcct tgtcatctgg agcccgaggc gttaccctag
4201 gtcttggggg tgatccgggg caaccgcctc ggtttcgcct ttttatgggt ccaaaataac
4261 cgtcagccca gcggctggca atccccctc ctaaaaggcc gttataggcc ctgctaggag
4321 ggggggtagta ctttcctacc ccctaggct tggagaggcc ttaggaggtc tcctagggcc
4381 tcgtgggggt gtaggggtaa cctcatggcc aggccggccg gctcgggact ctggaggagg
4441 cctccatagc ctactcgtgg tggaggtttg tgaaggggtt cactaatgca tacggctagc
4501 ctcgggatca cggccaaatg gtatgcaggt tttggtataa aaccctcagg tttgaggcta
4561 gtttatgtcg gtttatgca cctttgactc ggatcacggg cataaacacc agtttcctgc
4621 acgaaagaaa actttcgcga tctaagaggg ggaaagaggt gtagagggac ggccttcatg
4681 aaagttggcc tcttaggagg ccgttgtaga gggccgtctc gggttcaaat cctttccctc
4741 tctctccagg tttccgaggt tcgaggtctt ggtccaggtc ttgtaccaag tttttgacca
4801 aagtctattc tcggaatata gggtatctt gtctatcttc cctacgggat atctctgtct
4861 gtgtgaactt gatcccatcc caatacatat ctcaatctcc taatctcctc ttctctccag
4921 atccctaatc tcttcttcta cctctttctc ctcccaatta agaatggaga ggaaaaaccc
4981 cgaccagaac gagcttctcg gggtcagttt cggtaatctc gggacaggtt ttcatcgtct
5041 aggacgagga ttagggcatg aaaaatgggc tttgacaaaa tctttctaaa aaatactccc
5101 cgaggttggg gaagtgccct cggggagaag attttttggca gtttagatgt tatgctctat
5161 cacgggccgg aggcctccac gataagttgt cttggccaag taccgggcca ggtcgggggt
5221 gctcttcagc gtggtgatgg tactttcacg gaagttcaca agtcctttta gaggcttcag
5281 gtcggggata gtgctcaagt actcccaagc gttctcgggc ccgtggtcgg ggagaaggac
5341 aaaggggtcg ggcaaaagtt catctttgta cttaggacgg attactttag cacctgataa
5401 cttcagggcc gttaagaagg gcctcacctc ggagacgggt ggaaggagga cgtgggcgtg
5461 gaagaagacg aaccccgatt tttgggaagt ctccctccag tttgatgatg aacgttggga
5521 ggaagccggc caggatgtct ttcatcgcgc ctcgaacctc ggacacataa aaaactttcg
5581 tgtttgtcag ggcaagagtg ctatgtatga ggtaaccttc gggagtacaa agtgcctcaa
5641 gccgcctttc ccaacgctcc aaaactctag ggtcaggtgg tttaggtttt ctgaaaaact
5701 ctagcttttc agtggtcatt cctcacccct ctagcacgta ctctggaagg taaacctttg
5761 acacagcggc caagtctagc gtctcccagt ccagttggtc tgggacgcgt gagaagggga
5821 ggggcttggt gtagaggacc agaagaccc
```

FIG. 4

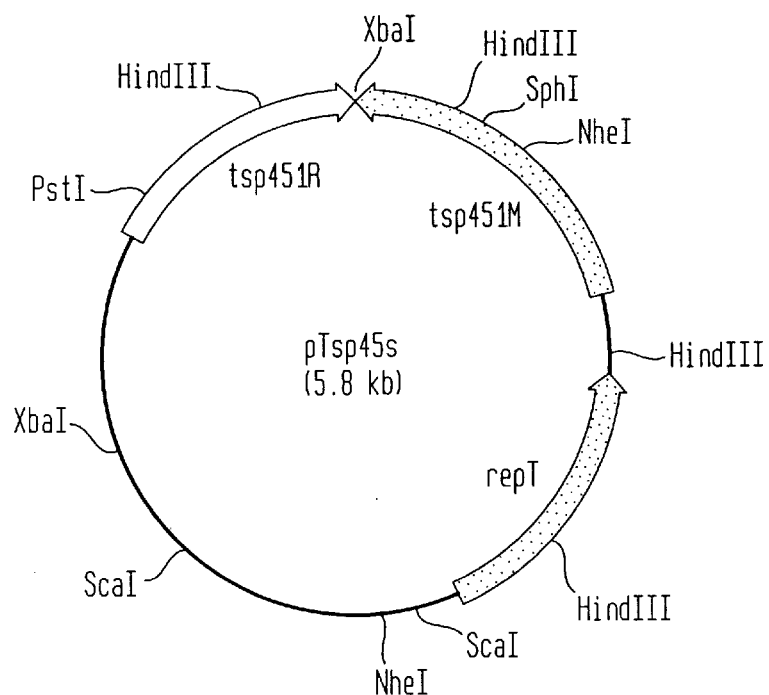

FIG. 5

```
  1 ATGATCGTGGCTGTCACCGGCTTCAAGGGAGGGGTGGGGAAGACCACCACGGCGGTCCAC
    M  I  V  A  V  T  G  F  K  G  G  V  G  K  T  T  T  A  V  H
 61 CTGGCCTGCTTCCTGGCCGAGCGGGGCCCCACCCTGCTGGTGGACGGGGACCCCAACCGC
    L  A  C  F  L  A  E  R  G  P  T  L  L  V  D  G  D  P  N  R
121 TCCGCCACGGGGTGGCACCGGAGGGGAGGCCTCCCGGTGACCGTGGTGGACGAGCGGGTG
    S  A  T  G  W  H  R  R  G  G  L  P  V  T  V  V  D  E  R  V
181 GCGGCCCGGTACGCCCGGGAGCACGCCCACGTGGTCATAGACACCCAGGCCCGCCCCACG
    A  A  R  Y  A  R  E  H  A  H  V  V  I  D  T  Q  A  R  P  T
241 GAAGAGGACCTCCGGGCCCTCGCCAAGGGGGTGGACCTGCTGGTCCTGCCCACGTCCCCC
    E  E  D  L  R  A  L  A  K  G  V  D  L  L  V  L  P  T  S  P
301 GACGCCCTGGCCCTGGAGGCCCTCCTGGCCACCCTGGAAGCCCTGCGGGGGGCGGAGGCC
    D  A  L  A  L  E  A  L  L  A  T  L  E  A  L  R  G  A  E  A
361 CGCTTCCGGGTCCTCCTGACCATGGTGCCCCCGCCCCCGAGCCGGGACGGGGAGGAGGCC
    R  F  R  V  L  L  T  M  V  P  P  P  P  S  R  D  G  E  E  A
421 CGGGCCCTCTTGGGGGCGGAGGGCGTTCCCCTCTTCACAGGCTGGGTGAGGCGGGCGGCA
    R  A  L  L  G  A  E  G  V  P  L  F  T  G  W  V  R  R  A  A
481 GCCTTCCCCAAGGCCGCCCTCCTGGGGGTGCCTGTCTACCGGGTGCCCGACCCCAGGGCG
    A  F  P  K  A  A  L  L  G  V  P  V  Y  R  V  P  D  P  R  A
541 AGGCTGGCCTGGGGGGACTACGCGCGGGTGGGGGAAGAGCTCCTGAAGGAGGTGGGGGGA
    R  L  A  W  G  D  Y  A  R  V  G  E  E  L  L  K  E  V  G  G
601 TGA 603
```

FIG. 7A

```
     CTTATACACACAAACTATACACGTCTCTATCGGGCTTTTCTTAGCGCCATGTAAAACACC
   1 ------------+----------+----------+----------+----------+----------+  60
     CCTCCCATCTCCGGGTGTTTACAGCGGATACGGGAGGTTCAGCGGGAACTTTTCCCCTTG
  61 ------------+----------+----------+----------+----------+----------+ 120
     TTGAAACTTTGGGGTCTGAGGCTCAACAGCAGAACAGCTTAGGTTGACTCAACACAGCTC
 121 ------------+----------+----------+----------+----------+----------+ 180
     ATAAGTCCCTTCATTATCGCCTGAGTCAACCTATGAGTTAACCTTTTTTCAAGAAAAAGA
 181 ------------+----------+----------+----------+----------+----------+ 240
     GATAAGTGAGTTTTGTCCTCTAGCACGACTTTTTTCTTTGAGTCAACCTCTGTGCCGACC
 241 ------------+----------+----------+----------+----------+----------+ 300
     CCCCCGATTTTGAGTCAACCCCCCTTTGAGCCGAAACTTTGTTGGCACAGGGGTTGACTC
 301 ------------+----------+----------+----------+----------+----------+ 360
     AGGGGTTGACTCAACGCGAATGGCCTCTGGAAGGGCGTTGAGCCGACCCCTCCCTCGTGT
 361 ------------+----------+----------+----------+----------+----------+ 420
     GCCGACCCCCGCTCCACTATGAGCAGGGGGGAAAGTTACGGGAAAAGTTCCCCAAGTCCC
 421 ------------+----------+----------+----------+----------+----------+ 480
     CCTTGACAAAAGATGACAATCGAGTTAATGTCACAGCGATGCGTCACTCACCTCTGGCTG
 481 ------------+----------+----------+----------+----------+----------+ 540
     GGCTCACCCAGATGCGTGCGCGAACGTTTCAGAGCCTCCTTCGATTCCTGGCCAGGGAGG
 541 ------------+----------+----------+----------+----------+----------+ 600
     GGCGCTACCCCACTGGTGTAGAGCTCGCCAAGGTGCTGGGGCGCAGCCCGCACGCCACGT
 601 ------------+----------+----------+----------+----------+----------+ 660
     GGGCCATGCTCAGGGCTTTGACCCGTCATGGACTCGTGGAACGGCACGAGGGGGTCTATG
 661 ------------+----------+----------+----------+----------+----------+ 720
     TTCTGACCCCTGCGGGCGTAGAACTTGCCAGGACCCTGGGAACCACCGTGTGGCGTGGGG
 721 ------------+----------+----------+----------+----------+----------+ 780
     ATGAGGAGGTACAGACGGCGTTACAGCTGCTAGGAGTCGGTCATGCCGCCGAGGACAGGC
 781 ------------+----------+----------+----------+----------+----------+ 840
     GCTGAAGCTTTTGAGCCGGGGCCCTCACCCAAGGCCACCCCGGCTCCTCTCCCTGGGAT
 841 ------------+----------+----------+----------+----------+----------+ 900
     CCCAAATGGATCCCTCAGCGCCATTATCCTCCTGGCGGTCCTATAGCGCAAGGAGGTAGT
 901 ------------+----------+----------+----------+----------+----------+ 960
     GGTGACGAAACACACAAATGTTTCACCCCACCTTTTGGATGCCGTAGAGGAGCTCGCTCG
 961 ------------+----------+----------+----------+----------+----------+ 1020
     CCAGATTGCTGAAACCGCTAACAAGGCTTATTCCAGCCATTTCAGGCAGATTGTCAAAGT
1021 ------------+----------+----------+----------+----------+----------+ 1080
     CCTGCCGCCTGAGGTTCCCGACCTCTACGCCTGGCTGGCCGCCCTGGATGACTCCGCCAT
1081 ------------+----------+----------+----------+----------+----------+ 1140
     CGAGGAGCTTGCCCAGCGCCTGAGGGAGGTCGAGGGAAGCCCCCGCCCCCATTTCACCGC
1141 ------------+----------+----------+----------+----------+----------+ 1200
     CGCCCTCAAAAAGGCCCTGGCCATCGCCCTACAGCGGCGGACCCTCGCCGAGATGCCCCC
1201 ------------+----------+----------+----------+----------+----------+ 1260
     CACGTTCGCCAACGCGCTCCGCTGGGCGATGGAACGGCAAGGGGTGAGCATCCGCAAGCT
1261 ------------+----------+----------+----------+----------+----------+ 1320
     TGCGAGAGAGGTAGGGGTCAGCAAAACCACTGTTAAAAAGTGGCGTGGAGGCCGCTTTGT
1321 ------------+----------+----------+----------+----------+----------+ 1380
     CCCTCGTTCACGGACCTACGTGAGGAGGTTGGAGGAGATCCTGGACCTCCCGGAAGGCGC
1381 ------------+----------+----------+----------+----------+----------+ 1440
     CCTTTCGGGACGACTACCCCGCTGGGGGTTGCCAAAAATATTGGAAGGTGTTGAGGGGAA
1441 ------------+----------+----------+----------+----------+----------+ 1500
     AGATGCCCCTTATCCCGGGTTCACGCGGACCTTCCTGCGCGTGGCCGCCCTGGCGCGCTA
1501 ------------+----------+----------+----------+----------+----------+ 1560
     CGGCCGCCCGTGGGATGATCTCTCTCCCGACGAACAGGAGGCCCTTCGGCGCGAGGACGA
1561 ------------+----------+----------+----------+----------+----------+ 1620
     AGACCGGTGGACCCGCCTCTCCAACCGCCAGAAGCGAGTGCGAAAGGCCAGTCAAAAACC
1621 ------------+----------+----------+----------+----------+----------+ 1680
     TTTTCGGCTTTCCTTTGACGAGTGGCCAACTGAGGCTCGCAAAGAATGGGAGGACTACGA
1681 ------------+----------+----------+----------+----------+----------+ 1740
     GCGCTATGCCTCATCGGCACCTGGGAGCATCGCGCGCGTGCAGGCGGCGCTTGCGGGCGC
1741 ------------+----------+----------+----------+----------+----------+ 1800
     ACCTCTCGCTCCCACGACCGTGCGGACGGAAACGCTCGAGCGTGAGCGGATACTTATAGA
1801 ------------+----------+----------+----------+----------+----------+ 1860
```

FIG. 7B

```
     ACTGTTCTACGGCTACTGTGTAAACGAACGGGGCCTCGACAGCAACGCGTTGAGCCTCGC
1861 ------------------------------------------------------------ 1920
     CCTCCTCACAGACCTGGAGCTCGTCCAATCGTACCTGGAGTGGCGCGTGAATAGGTACAA
1921 ------------------------------------------------------------ 1980
     GGACGAGGATTTACCCCCCGTTACTCGATCGGAATACATGTTTATCGCCCTGGTGAAAAA
1981 ------------------------------------------------------------ 2040
     ACTCCACAGAGGTTATCTCCGCGCCCTTGGGCTTGGGGTAGACCCGGACGGGGTGAAAGA
2041 ------------------------------------------------------------ 2100
     GCTGGAACGGAAACTGAAAATCGCCGGAATTGATGTCACGGACGGCTACCACGCGGTGGA
2101 ------------------------------------------------------------ 2160
     GCCCCTCCTGGAAACTCACGAGCCCCTCCGCTGGGTGCTGGATGGCATCCGGCTCATGCT
2161 ------------------------------------------------------------ 2220
     CCGCGATGCGGCGGGGCGGGTAGGCAACCTGCTGACACCCCAAATCCCCACCGCCAAAAG
2221 ------------------------------------------------------------ 2280
     CGAAGCGGGCGAAGCGTTCGCCCTCTACCGGGACGTCGTTCTGCTTTGGATGATGGTGGG
2281 ------------------------------------------------------------ 2340
     CCACCCCCTCCGGGCGAAGCATTACTACGAAGCTCGCTTGGACATGAGCCAGTTCCAAGA
2341 ------------------------------------------------------------ 2400
     CGGGGATTTCGCTCCCGGGCGGGGACACGTGGGGCGGGCCGGCGGAGGGTACTACCTGGC
2401 ------------------------------------------------------------ 2460
     CTACCGCAAAGTGGAGTTCAAAAACGCCCGAGGCCAGGTCTTTCAGAGCCTCCAGGACCA
2461 ------------------------------------------------------------ 2520
     CGATCTCGTCACGTTCCCCCTGGACGACCCCGAGCACCCTGTCCTGGTCCTGGACGTGAA
2521 ------------------------------------------------------------ 2580
     CGGGATGCGGTACTCCCTCAACGAGCTCTTTCACGTCTACCTGCGCACGATCCTCTCCCG
2581 ------------------------------------------------------------ 2640
     CCTGGCCCAGGCCTGGGCCGGACCGGTCCCCTCCTGCCCCTGTTTCCGGGTGCCGATACG
2641 ------------------------------------------------------------ 2700
     AGGCTCAGACTTGCGCACATCGTTCGCAGGCGCGCCGCCTACGTGGCCGCCGTGCCCGGG
2701 ------------------------------------------------------------ 2760
     GTACCCCAGAAACTTTTGCCCTTCGGCCCCCACTCCATCCGCCACGTGGTGGCCACGGAG
2761 ------------------------------------------------------------ 2820
     GTCGTGAAGCGCACGGGCTCTTTTGAGGCCGCCGCCAACGTGCTCCTGGATAGCATAGAC
2821 ------------------------------------------------------------ 2880
     ATGGTCGTTCGACATTACGCCCGTTCGTTCCCCGCGACCGTAACAGTCACGGTTGGCGGG
2881 ------------------------------------------------------------ 2940
     CTAACGCCCGCGCCCGGGGAGGTGAGCGGTGAGGGACCTCCACGACTTTTTCCTGGCCCG
2941 ------------------------------------------------------------ 3000
     GGTGGACGAACTGGTGCCGGAACTCCTACCCGGGGCGCGGCGGGTGGGCGACGAGTGGCG
3001 ------------------------------------------------------------ 3060
     GGCGGGCTCGGTCCAGGGCGAGCGGGGCGACAGCCTGGCCGTGGACCGCGGGAAGGGCTT
3061 ------------------------------------------------------------ 3120
     CTGGATCGACCACAACCCCTCGGCCCCCGAGCCCCGGCAGGGAAACCTCCTCACGCTGAT
3121 ------------------------------------------------------------ 3180
     CCAGGCGGCCAAGGGGCTCTCCCCCGAGGAGGCCCGGCGCTGGGCCCAGCAGTGGCTTGG
3181 ------------------------------------------------------------ 3240
     CCTCTCCCCTTCGCCAAAGGTCAGGCGGACGAGGAGCTCAGGACCAAAGGTCTTGAGTAC
3241 ------------------------------------------------------------ 3300
     TCAAGTGCGTGGGAGCTCGGGTGCTCCAGTCCCTGAGTCTTCAGGTTCCCAGGTACCTGA
3301 ------------------------------------------------------------ 3360
     GGAGTCGGACCCCTTTGACAACCCCCGCTTCCGGGACCTCCTCACCCCCAGGGGCGAGGA
3361 ------------------------------------------------------------ 3420
     CGAGGCCCCCTTGGCCCCCGGCCTCCGAGGAGGTGCTGCGGCGCATGGTGTCTAGGCTTCT
3421 ------------------------------------------------------------ 3480
     CCGCACCCCCGAGGCCGTGGCCTACCTGAAGGGGCGCGGTCTGGATGCCCGGGTGGTCCG
3481 ------------------------------------------------------------ 3540
     CCGCTTCTACCTCGGCCTGGACGACACCGCGCGGGCCACCGCCGCCCTGGTCTACCCGGT
3541 ------------------------------------------------------------ 3600
     GATAGGGCCGGACGGCTCCCCCGTTCGCCGCCACCTCTACTACGAGATCCCCGGCCTCAC
3601 ------------------------------------------------------------ 3660
     CCAGGGCGCCCCGGGCAAGGGCTGGGGGAGGGGGAGGCCCACCAGCTACTGGGCCCTCCC
3661 ------------------------------------------------------------ 3720
```

FIG. 7C

```
       CCCCTTCGAGGGCCCCTCCCCCCGCCGCAAGCTCTTCTTGTGCGAGGGGGCGAAGGATGC
 3721  ------------------------------------------------------------  3780
       CTGGGCCCTCTGGCTCCACCTCCACGCCCAGCCCTGGGCCCAGGACCTGGCGGTGGTGAC
 3781  ------------------------------------------------------------  3840
       CTCCACGCACGGCTCCGCCCTCCCCGAGGCCTGGAAAGACCCCCTGTTCTGGGCCCCTTG
 3841  ------------------------------------------------------------  3900
       GGAGGAGGTCTACCTGGGCCAGGACGCCGACTCCGCCGGCGAGGAGATGGCCCGGAAGGT
 3901  ------------------------------------------------------------  3960
       GGCGGAGGTGGCGAGGCGGCCCGTCCGCCGCGTCCGGGTCCCGGAGGGGATGGGGAAGGA
 3961  ------------------------------------------------------------  4020
       CTGGACGGACTACTTCCTGGCGGGGGGCACCCCCGAGGGCTTGCGCCTCCTCCTGGAGGG
 4021  ------------------------------------------------------------  4080
       AGCGGAGGTCTGGGAAGAAGAAGTGGCTGGAGGTGGGGCCAGGATCCAGCTCCCGGACCC
 4081  ------------------------------------------------------------  4140
       CGTGGACATCCAGCGGGCCTTCGTGCGGGGCCACCTCTACGTCCCCGTGCGGGTCCTGGA
 4141  ------------------------------------------------------------  4200
       GAACCGGGGGGAAGAAGGGGCCCGCTACCGCACCGTGGTGGTCCGCTCCGACGGGGCCGT
 4201  ------------------------------------------------------------  4260
       CCTGGGCTGGGGCTACTTGCCGGCCCCGCCCGGCACCCCCTTGGAGGACCGGGTGCTGGC
 4261  ------------------------------------------------------------  4320
       CGTGGACGACGGCACCATCATCCGCAGGCCCCCGAAGGCGGCCGCCGGGACCTCGTGGAA
 4321  ------------------------------------------------------------  4380
       CGGGGAGGCCATCAACCGCTTCCTGGAAGCCCGGGCCCGGGGAGTGAGCGCCATGACCGT
 4381  ------------------------------------------------------------  4440
       GGCCCCCCGGGACCTGCCCTGGGCTCATCGTCCGCCACCTCCGCCAGGTGATCCTCCCCAG
 4441  ------------------------------------------------------------  4500
       TGAGGACGGCTACCTCCTGGCCGCCTTAGGGGTCATGACCTCCTACGTGCAGAGCGTCTT
 4501  ------------------------------------------------------------  4560
       CGACGCCGTGCCCCTCTTCCTCGTGGTGGGCCCGCCGGGCTCGGGGAAGACGGAGTTCGC
 4561  ------------------------------------------------------------  4620
       CCGCCTCATGGCCGAGCTGGGGGCCAACGGCGTGGTGATCACCGGCCAGACCTCCGCCGC
 4621  ------------------------------------------------------------  4680
       CACCGCCGCCCGGATCATCGACGAGACGGGGGGGCTGGTGGCCTTCGACGACCTGGAGGA
 4681  ------------------------------------------------------------  4740
       GGTGCGCCAGCGGTCGGGGAGCGCTGAGGCCTCCCAGCTGGAGCAGTTCCTCAAGGTGTC
 4741  ------------------------------------------------------------  4800
       CTACAAGAAGGAGACCGCGGTCAAGAGCTGGACGGACACCAAGGGGATGCGGGTCCTCAC
 4801  ------------------------------------------------------------  4860
       CCTCAACTTCTTCGGGGTCAAGGTGATCACCAACACCCAGGGGACGGGGGACATCCTGGG
 4861  ------------------------------------------------------------  4920
       GAGCCGGATGCTGGTCATCCGCACCGCCCGCCTCCGGGACCTGGGCAGAGGGGAGGAGCG
 4921  ------------------------------------------------------------  4980
       CCGCCCCGAGGGGCTCTCCCCCCCAGGCCCTCCAAGAACTCCGGGACAACCTCTACATCT
 4981  ------------------------------------------------------------  5040
       GGGCCATGGAGAACGCGGCCAGCCTCCACGCCCTGTACCGGGAGCGCTTCGCGGGCAAGG
 5041  ------------------------------------------------------------  5100
       GGGAGCGCCTGGACGAGATCGCCGCCCCCTTGCGTACCATCGCCCACCACCTGGGGGACG
 5101  ------------------------------------------------------------  5160
       AGGAGCTGGCGGCCCGCCTGGAGGACGCCCTGCGCCGGCAGGAAGGGCGCCTGGAGGAGA
 5161  ------------------------------------------------------------  5220
       CCCTTTCCGATGCCGAGGTGGTGGAGACCGCCCTCAAGGAGGCCATCCGCCAGGGCTACC
 5221  ------------------------------------------------------------  5280
       GGAGCCACGTGGCCCTGGTCCACGTGATCTTCCAGGCCCGGAAGATCTTCGGGGACGACT
 5281  ------------------------------------------------------------  5340
       GGGGCCGGGAGCGCACCGTGGACATCCCCCGGTGGCGGGACCCCAAGTGGGTGGGGCAGA
 5341  ------------------------------------------------------------  5400
       TCGCCAGCAACTACGGCTGGGCGGCCCCAGAAAAGGCCCGTGAGGCCCCGGCTTTGGGACA
 5401  ------------------------------------------------------------  5460
       AGCAGTTCCGCATCATGCGCCTGGAGCCCACCTTCGTGGAGCGGGTGGTCAGGGGCTTCC
 5461  ------------------------------------------------------------  5520
       TCCAGGAGGGGATCCCCTTGGAGCCCCTGAAGCAACCCCTGGCTTCTGCCTGGACACCCC
 5521  ------------------------------------------------------------  5580
```

FIG. 7D

```
      CTGCGCCGAGTGCGCCTACCTGCACTGGTGCGACCTCCGGCCTGACAAGGAAAAGTGGCT
5581  ------------------------------------------------------------  5640
      GGAGCGCTACGGGGAGGCCAAGCTGGCCCAGAAAAGGCGGGAGCTGGAGGAGGAGTTTTT
5641  ------------------------------------------------------------  5700
      GGCCCTGGTGGGGCCCCAAGATGGCCTTGGCCTCCAGGCTTCCGCCGAGGAGGAGGGAGA
5701  ------------------------------------------------------------  5760
      CCGAGGTAAGCACCCAAGTACCCAAGTACCCAAGACCCTAAAGCCTCAGGTACCGGAGGA
5761  ------------------------------------------------------------  5820
      CCTCGGGGACGGAGGACCTAAAACCCCAAGGGCGTGAAAGACTGAGGTGAGAGGGATGAT
5821  ------------------------------------------------------------  5880
      CGTGGCTGTCACCGGCTTCAAGGGAGGGGTGGGGAAGACCACCACGGCGGTCCACCTGGC
5881  ------------------------------------------------------------  5940
      CTGCTTCCTGGCCGAGCGGGGCCCCACCCTGCTGGTGGACGGGGACCCCAACCGCTCCGC
5941  ------------------------------------------------------------  6000
      CACGGGGTGGCACCGGAGGGGAGGCCTCCCGGTGACCGTGGTGGACGAGCGGGTGGCGGC
6001  ------------------------------------------------------------  6060
      CCGGTACGCCCGGGAGCACGCCCACGTGGTCATAGACACCCAGGCCCGCCCCACGGAAGA
6061  ------------------------------------------------------------  6120
      GGACCTCCGGGCCCTCGCCAAGGGGGTGGACCTGCTGGTCCTGCCCACGTCCCCCGACGC
6121  ------------------------------------------------------------  6180
      CCTGGCCCTGGAGGCCCTCCTGGCCACCCTGGAAGCCCTGCGGGGGGCGGAGGCCCGCTT
6181  ------------------------------------------------------------  6240
      CCGGGTCCTCCTGACCATGGTGCCCCCGCCCCCGAGCCGGGACGGGGAGGAGGCCCGGGC
6241  ------------------------------------------------------------  6300
      CCTCTTGGGGGCGGAGGGCGTTCCCCTCTTCACAGGCTGGGTGAGGCGGGCGGCAGCCTT
6301  ------------------------------------------------------------  6360
      CCCCAAGGCCGCCCTCCTGGGGGTGCCTGTCTACCGGGTGCCCGACCCCAGGGCGAGGCT
6361  ------------------------------------------------------------  6420
      GGCCTGGGGGGACTACGCGCGGGTGGGGGAAGAGCTCCTGAAGGAGGTGGGGGGATGAGC
6421  ------------------------------------------------------------  6480
      AAGTTCGCCAGGCTCCTCAAAGAGGTCAAGGAGAAGGAGGAGGCCTCCGGGGAGCGGCCT
6481  ------------------------------------------------------------  6540
      CGGGGGAAGAGCCGGCGGGAGGACTACGTGGCCATGAAGGTCTACATCAGCAAAGAGCTT
6541  ------------------------------------------------------------  6600
      CACCGGAGGCTGAAGCTGAAGGCCCTGGAGGAGGAGAAGGAGCTTTCGGAGCTGGTGGAA
6601  ------------------------------------------------------------  6660
      GAGGCCCTGAGGAAGTTGCTGGTGTGACCTCCTCCCGCCTCGTAGAGCGTGAAAAGGAGG
6661  ------------------------------------------------------------  6720
      TAAGACGATGGTCACCCTTAACAAATCGCCCCTAGAAGCCCTCTACGCGGGCCACTCCCC
6721  ------------------------------------------------------------  6780
      CCAGGAGGCGGGCCGTCTCTTCGAAGCGCCTGGTCCGCAAGATATTGAAGGAACTCCACC
6781  ------------------------------------------------------------  6840
      CCATCTGGAGCCAAGAGTTCGTGGATGTCGTCCCTTGGTCCGAGCACGCCACCCGCAAGG
6841  ------------------------------------------------------------  6900
      GGCTCAGGGCCACGGACATCGGCGTGGACCTGGTGGGCTACGGGAAGGACGACAAGGTCT
6901  ------------------------------------------------------------  6960
      ACGCCATCCAGGTCAAGCTGTGGGATAAGCCCCTCTCTTGGAAGGACCTGGGGAGCTTCG
6961  ------------------------------------------------------------  7020
      TGGGGGTGGTGAACCACCCCGAGTACGGCTTCGACCACGGGCTCATCGTGGCCCCAAGAG
7021  ------------------------------------------------------------  7080
      GCGTGACCCAGGAGGCCGACCGCCAGCTCCAGGGCCTACCCATCACCATCCTGAGCGAAG
7081  ------------------------------------------------------------  7140
      AGGCTCTCCTAGAAGACCTGGACCTGGAATCCCTCGTTCCAGACCGCCCCGAGGAAGCCC
7141  ------------------------------------------------------------  7200
      GCAGGCGGGGGAAGAAGGCCCTCCGTAAGTACCAGCAAGAAGCCTTAGAGGAGGTGGCCA
7201  ------------------------------------------------------------  7260
      AAGCCTTCTTAGAGAAGGGCCTGCCCCGGGGCAAGCTCATCATGCCCCCGGGCACGGGCA
7261  ------------------------------------------------------------  7320
      AGACCCTGGTGGCCCTCAAGATCGCCGAAAAGGTGGCGGGCCCCGGGGGGAGGGTCCTCT
7321  ------------------------------------------------------------  7380
      TCCTGGCGCCCTCCATCGCCCTCCTGGACCAGTCCCTCAGGGCCTGGGCGGCGGAGGCTT
7381  ------------------------------------------------------------  7440
```

FIG. 7E

```
         CCTTGCCCTTGCGCCTCTTCGCCGTGGTCTCGGACACGGGCGTGGGCAAGACCTCGGAGG
    7441 ------+---------+---------+---------+---------+---------+ 7500
         ACGACCTCTCCGCCCTCTCCCTCCTCTCCATCCCTCCTACCACCAAGCCTGAGGAGCTGG
    7501 ------+---------+---------+---------+---------+---------+ 7560
         CCTCCGAGGCCAAGACGGAGAGTCAGGAGGCCCTCACCGTGGTCTTCTCCACCTACCAGT
    7561 ------+---------+---------+---------+---------+---------+ 7620
         CGGCGGAGGTCCTGGAGAGGGCCCAGAAGGAGCACGGGCTTCCCCCTTTTGACCTGATGA
    7621 ------+---------+---------+---------+---------+---------+ 7680
         TCCTGGACGAAGCCCACCGCACAGCCACGGTGCGGGCGGGAGAAGAAAGCCCCTTCACCA
    7681 ------+---------+---------+---------+---------+---------+ 7740
         AGGTGCACCACGACCACTACGTGAAGGCCCGCCACCGCCTCTACATGACGGCCACGCCCA
    7741 ------+---------+---------+---------+---------+---------+ 7800
         GGATCTGGGAGGTGGAGGGGAATGGAGAGAGGGGCCAAGGGAAAAAGGCGGGGAAAAAGA
    7801 ------+---------+---------+---------+---------+---------+ 7860
         AGGACCCTCAGAAAGAGGGTTCTCCTCCCCTTTTGGACCTCGGTGCCTCTCCTACGGAGG
    7861 ------+---------+---------+---------+---------+---------+ 7920
         ACTCCACGGCCCCCGAAGGGGTGGAACTCCTGGTCTACTCCATGGACAACGAGGGGATCT
    7921 ------+---------+---------+---------+---------+---------+ 7980
         ATGGCCCCACCCTCTACGAGTACACCTTCACCCGCGCCGTGAAGGAGGGCCACCTGAGCG
    7981 ------+---------+---------+---------+---------+---------+ 8040
         ACTACAAGGTCATCGTCTTCTCCGTGGCGGAGGAAGCCCAAAAGGACCTGGCCTCCTACC
    8041 ------+---------+---------+---------+---------+---------+ 8100
         TCCAGGGACCCGAGGCCCTCAAGGTGGAGGAGGCTCTGAAGGCCCTGGGCCTGTGGAAGG
    8101 ------+---------+---------+---------+---------+---------+ 8160
         TCCTCCAGGGGGAGGTGCGGGACGAGGAGGGGAACCCGATGGGGGGCCTCGACCTGCGGA
    8161 ------+---------+---------+---------+---------+---------+ 8220
         GAGTCATCGCCTTCCACGGCCGGGTGAAGGAGTCCAAGGAGATGGAGGAAGAGTTCACGA
    8221 ------+---------+---------+---------+---------+---------+ 8280
         AGGTGGCCCTCGCTGCCCAGCAGGCTGGCCTCCTTCCCGAGGAGCTCCGGCGGGTGGAGG
    8281 ------+---------+---------+---------+---------+---------+ 8340
         TGAAGCACATAGACGGGCAGATGTCCGCCTATGACCGGAAGCGCCTCCTGGACTGGCTTA
    8341 ------+---------+---------+---------+---------+---------+ 8400
         GGGAGAACGTCCCCGAGGGGGAGGTCCGCCTCCTCACCAACGCCAAGGTCCTCACCGAGG
    8401 ------+---------+---------+---------+---------+---------+ 8460
         GGATCGACGTCCCCGGCCCTAGATGCCGTGGCCTTCATGCGTCCCCGGGACAGCGTGGTGG
    8461 ------+---------+---------+---------+---------+---------+ 8520
         ACGTGATCCAGGCCGTGGGGCGGGCCATGCGCAAGGCCCCGGGCAAGGAGTACGGGTACG
    8521 ------+---------+---------+---------+---------+---------+ 8580
         TGGTCCTGCCCGTGGTGGTGAGGGGGCAGGACGAGGAGCGGGAGATCGAGGAGAGCGGCT
    8581 ------+---------+---------+---------+---------+---------+ 8640
         ACCGGGCGGTGTGGCAGGTGCTCTCGGCCTTGCGCTCGGTGGACAAGTCCTTCGAGGCCC
    8641 ------+---------+---------+---------+---------+---------+ 8700
         GCATGCGGGCCGCCCTGGTGCGCCTCTCGGGTAAGGGCGAGGGCGGGGAAGGTGGAGAGG
    8701 ------+---------+---------+---------+---------+---------+ 8760
         CCCGAGAGGGTGTGGCCGTCATCGGGGAAGGAAGCGCCTCCCCCGTGATCGTAGATGTCC
    8761 ------+---------+---------+---------+---------+---------+ 8820
         TTCAGGGGAACCTCAACCTCCACCAGGAGATCACCCGGAGCCTCGCCGGCAAGCTGGTCA
    8821 ------+---------+---------+---------+---------+---------+ 8880
         GGCGCCTCGCCCTGGGGCGGAAGTACCTGGAGAACTGGGCCCAGGACGTGGCCCGGGTGG
    8881 ------+---------+---------+---------+---------+---------+ 8940
         CGAAGGTGCTGGAGCAGCAGGTCAGGGCGATGGCGGAGCGGGACCCCAAGGTGAAGGAAA
    8941 ------+---------+---------+---------+---------+---------+ 9000
         AACTGGGGAAACTCCTCGCCGCCCTGCAGGCCTTCACCAGCGAGAGCGTGACGGAGGACG
    9001 ------+---------+---------+---------+---------+---------+ 9060
         AAGCCATCCTCATGCTGGTCCAGCACGCTCTCACCAAGCCCATCTTCGACGCCCTCTTCG
    9061 ------+---------+---------+---------+---------+---------+ 9120
         GGGAACTCCTAGAAAAGCGGGAGGACCCCGTTTCCCGGGCCCTAGACGAACTCTTCCAGG
    9121 ------+---------+---------+---------+---------+---------+ 9180
         AGTTCAGGGGGTTCCTGGACCGGGAAGGGGAGGCCCTCAAGGATTTCTACGAAGAGATGC
    9181 ------+---------+---------+---------+---------+---------+ 9240
         GCCTCAAGGCCCTAGGGCTCACGGACGAAGCCGAAAGGGCCGACTTCCTACGGAGGCTCT
    9241 ------+---------+---------+---------+---------+---------+ 9300
```

FIG. 7F

```
      ACTCCAACTTCTTCGCCCGGGCCTTCCCCCAGGTGGCCGACCAGGTGGGGATCGCCTACA
 9301 ------------------------------------------------------------ 9360
      CCCCGGTGGAGCTGGTGGACTTCCTGGTGAAGAGCGCAGACGAGCTGGCCAGGAAGCACT
 9361 ------------------------------------------------------------ 9420
      GTTGGCCGGGGGCTCGATGGGGAGAAGGTCTTCATCCTGGAGCCCTTCGCCGGCACAGGC
 9421 ------------------------------------------------------------ 9480
      ACCTTCGTCACCCGAATCCTGCACCGGGTAGCCGAAAGGGGCGGGGCCGACGCGGTCAAG
 9481 ------------------------------------------------------------ 9540
      GGCAAGCTGGAGCGGGGGGAGATCTGGGCCAACGAGATCCTTCTCCTCCCCTACTACGTC
 9541 ------------------------------------------------------------ 9600
      CTCAGGGCCAACGTGGAGAACACCACCCTGGCCCTGACCGGGGAGTACGTCCCCTTCAAG
 9601 ------------------------------------------------------------ 9660
      GGGGCGTTCTGGCGGACTCCTTCGGCTGGCGGAGCTGGGGTATAGCGAGAAAAAGTTTGG
 9661 ------------------------------------------------------------ 9720
      CATCATCCCGCTCTTCCCGGAAGAATACGGTGAGGCCCTGAACGAGCAGCTGAAGGCCCC
 9721 ------------------------------------------------------------ 9780
      TATCCAGGTTATCCTCTCCAACCCCCCGTGCGGGCTTGGTTGGAGAAGGAGGGCGAGGGG
 9781 ------------------------------------------------------------ 9840
      AAGAAGAACCCCGTCTACCGTAAGGTGCGGGAGCGGGTGGAGCCAACCTATGTACGGCGG
 9841 ------------------------------------------------------------ 9900
      GCCAAGGAACTTCCCATCGGGGGGACAAAACCCAAGGGAGAGAACCTGAACTCCCTCTAC
 9901 ------------------------------------------------------------ 9960
      GACCAGTACATCCAGGCCTTGCGGGTGGCGAGCGACCGTATCGGGGAGGAGGGGTCGTG
 9961 ------------------------------------------------------------ 10020
      GCCTTCGTCACCAACAACGGGTGGCTGGGGGGCGTAGTGCCCCGGGGCTTGCGGGCCTCT
10021 ------------------------------------------------------------ 10080
      TTGGCGGAGGAGTTCGCCGAGGTGTACGTCTACGACCTGAGGGGGGATGCGAGGGAGAAG
10081 ------------------------------------------------------------ 10140
      GGGGAGGCACGGAAGAAGGAGGGGGCGGGGTCTTTGGACAGCCTTCCCGCGCCGGGGTC
10141 ------------------------------------------------------------ 10200
      TGCCTCCTCCTCCTGGTGAAGCGTAAGGACCACAAAGGGATCGGCAAGGTCCACCTCTAT
10201 ------------------------------------------------------------ 10260
      CGGGTCGGGGACGGCCTCTCCCGGGAGGCCAAGCTGGCTCTGGTGAAGGAGCATGGCTCA
10261 ------------------------------------------------------------ 10320
      GTCTCTGGGTTCCCTGGCAAGAGGTTCCCTATGAAGAGTGGGTGGGGAGGCTTACCCCCG
10321 ------------------------------------------------------------ 10380
      GGTTCTCGGGGATGTTGTCCCTGGACGAGGTCTTTGAGGTGCGGAGTTCTGGGGTGAAGA
10381 ------------------------------------------------------------ 10440
      CCAACCGCGATGCCTACGTCTTCAACCCCTCCCGGGCGGAGCTGGAGCGGCACATGAGGC
10441 ------------------------------------------------------------ 10500
      GGCTCATCTCCACCTACAACGAGCACGTGAAAAGGAAAAAAGAGGGGAAACTAGGGGAAC
10501 ------------------------------------------------------------ 10560
      TGGAAAAGGATGAGAGCATCATCAAGTGGGATAGGGAACTCATCAGGTACCTAGAGTCCC
10561 ------------------------------------------------------------ 10620
      TGAGGGAAGCTTCCTACGAAGGGAGCGGTCAAGTCTACGAGGCCCTCTACCGCCCCTTCG
10621 ------------------------------------------------------------ 10680
      TGCCTATGTACCTCTACCTCAGCCGCACTTTCAATAGCATGATTTACCAAATCCCCCGCA
10681 ------------------------------------------------------------ 10740
      TCTGGCCCACCCCCGAGGCCGAGAACCTGGCCATCGCCGTGGCCGGAAAGGGGAGTAACG
10741 ------------------------------------------------------------ 10800
      CTTTTAGCGCTGTGGCCACCAGGAGGGTGGTTGACCTGCACTTTATTGAGACCACCCAGC
10801 ------------------------------------------------------------ 10860
      TCTACCCCCTTTACCACTACCCCGAAAACAGCCCTCTGGGGGGACACCCAAAGCGCAAGC
10861 ------------------------------------------------------------ 10920
      TCAACCTCAAGGAGGAGTTCTTGAGGAAGCTTGGGGAGGTCCTCGGCCGCCCCGTTCCCC
10921 ------------------------------------------------------------ 10980
      CCGAGGAGGCCTTCGCTTACATCTACGCCGTGGTGAGCCACCCCCTCTACGCCGAGCGCT
10981 ------------------------------------------------------------ 11040
      TCGCCAAGGACCTCAAGATGGACCTCCCCCGCATTCCCCTCCCCCAAGATCCCGAACTCT
11041 ------------------------------------------------------------ 11100
      TTGCCAGGCTGGTGAAGGCGGGTCAAGAACTCATTCACCTCCACACCGAGTACGAGACCC
11101 ------------------------------------------------------------ 11160
```

FIG. 7G

```
           TGCCCCCCTGGAGCCCAGTCCCCCTTCGGGTGGAAGAGGGAGGCCCGGAGGACCCTACGA
11161      ------------------------------------------------------------  11220
           GCGCTACCGGGTGGAGCGGATGAGGCTGGACAAGGAGAGGAGGGTTCTCCAGTACAACGA
11221      ------------------------------------------------------------  11280
           CTGGGTCCGGGTGGAGGGCATCCCCGAGGAGGCCTTCCGCTGGCGCCCCGGGGGGTACTC
11281      ------------------------------------------------------------  11340
           CCCCTTGGAGTGGATTGGCCGCTTCTGGAAGGTGGAGGAGAAGGTGCCCAAGGGCAGGGG
11341      ------------------------------------------------------------  11400
           GGAGGCCATCGTCTGGGACCCCAACCTCTTCCTCAAGGAGAAGGGGGAACCCCGTTACCT
11401      ------------------------------------------------------------  11460
           CCTGGACCTCATCGGGCGGGCGGTCCAGGTGGCCGTGCAGACGGTTGGGATCCACGAGGA
11461      ------------------------------------------------------------  11520
           GCTGAGAGAAGACGTGGAAGCTCTGCTGGGTTGAGGGGGTGCTGGCCCGCCGTTCTCCCT
11521      ------------------------------------------------------------  11580
           ACTCCTTTAGGGCCTACCCCTACGATCCAAGCACGGCCCTGGGGGGCGCTCAGGTGGGCA
11581      ------------------------------------------------------------  11640
           TCCCACGTCCAAGGCCCCGACTTGGGCACCCCATGCTGCGAACTTACAGCCCAAGGGCCT
11641      ------------------------------------------------------------  11700
           GAAACATTCCCCCCTGCTCACGGGGGAAAGTTCGTGAAGGAAAGAGCAAAGCCTTTTTTA
11701      ------------------------------------------------------------  11760
           TCGCATCCGGAGAGATGGCGGGGTGGAACTTTTCCCCGAGGACTCCCCCATAGGGACATG
11761      ------------------------------------------------------------  11820
           TAAACGGCAAGCTATCAGTGTAGACTTTTTTCAAAAAGAGCCATACTCGTGTTTTCCCGT
11821      ------------------------------------------------------------  11880
           TCAGAACGGCATTTTTGCTAAGGAGGTGGTTTACAAATGGGTGTTAATGCGCTACATCCT
11881      ------------------------------------------------------------  11940
           CCGGTAGTAGGAGCATGC
11941      ------------------  11958
```

METHOD FOR CONSTRUCTION OF THERMUS-E. COLI SHUTTLE VECTORS AND IDENTIFICATION OF TWO THERMUS PLASMID REPLICATION ORIGINS

BACKGROUND OF THE INVENTION

The present invention relates to recombinant DNA molecules encoding plasmid DNA replication origins in Thermus, as well as to shuttle vectors which contain the same.

Many species of bacteria contain small circular extrachromosomal genetic elements, known as plasmids. Plasmids have been found in a number of bacteria which live in extreme environments, including the thermophiles, which live at high temperatures of more than 55° C. (Munster et al., *Appl. Environ. Microbiol.* 50:1325–1327 (1985); Kristjansson and Stetter, in 'Thermophilic Bacteria', Kristjansson, ed., p. 1–18 (1992)). However, most thermophile plasmids remain 'cryptic' in that functional genes have not been isolated from them, hence leaving their functional significance speculative (Hishinuma et al., *J. Gen. Microbiol.* 104:193–199 (1978); Eberhard et al., *Plasmid* 6:1–6 (1981); Vasquez et al., *FEBS Lett.* 158:339–342 (1983)). Common genes found in plasmids include those encoding plasmid replication and cellular maintenance, antibiotic resistance, bacteriocin production, sex determination, and other cellular functions (Kornberg and Baker, 'DNA Replication', $2^{nd}$ ed. (1991)).

It is often particularly difficult to cultivate thermophilic bacteria within the laboratory. They require high temperatures and often-unknown environmental conditions for acceptable growth (Kristjansson and Stetter, in 'Thermophilic Bacteria', Kristjansson, ed., p. 1–18 (1992)). However, with the advent of genetic engineering, it is now possible to clone genes from thermophiles into more easily cultivatable laboratory organisms, such as *E. coli* (Kristjansson, *Trends Biotech.* 7:349–353 (1989); Coolbear et al., *Adv. Biochem. Eng. Biotech.* 45:57–98 (1992)). The expression of such genes can be finely controlled within *E. coli*.

A *Thermus-E. coli* shuttle vector would be desirable if one needs to have the convenience of cloning in *E. coli*, isolation of DNA from *E. coli* for further manipulations and subsequently gene selection and expression in Thermus. Such *Thermus-E. coli* shuttle vectors could be used to screen, select and express thermostable proteins in Thermus. Using these vectors, a gene could, for example, be mutated within a mesophile, transferred to a thermophile, and then its encoded protein selected for increased thermostability. In this way, mesophile-thermophile shuttle-vectors can be used to conduct directed evolution, or protein engineering, on desirable gene products.

There is commercial incentive to produce thermostable proteins which are usually more thermostable in denaturing conditions then mesophilic counterparts (Wiegel and Ljungdahl, *CRC Crit. Rev. Biotech.* 3:39–108 (1984); Kristjansson, *Trends Biotech.* 7:349–353 (1989); Coolbear et al., *Adv. Biochem. Eng. Biotech.* 45:57–98 (1992)). These thermostable enzymes can also be used in a variety of assays, such as PCR, restriction enzyme-mediated PCR, thermo-cycle DNA sequencing and strand-displacement amplification, in which high temperatures are desirable. The shuttle vectors of the present invention should facilitate production of such thermostable proteins.

SUMMARY OF THE INVENTION

The present invention relates to recombinant DNA molecules encoding plasmid DNA replication origins in Thermus, as well as to shuttle vectors which contain the same.

Mesophile-thermophile shuttle vectors require origins of replication (oris) to be genetically maintained and transferred within each bacterial species. To construct appropriate mesophile-thermophile shuttle-vectors, restriction digested thermophile plasmid DNA fragments were ligated into the mesophilic vector pUC19-$Km^R$ (the thermostable $Km^R$ marker can be selected at 50°–65° C.). Plasmid pUC19 uses the ColEI ori to replicate within *E. coli* and does not replicate within the plasmid-accepting thermophile *Thermus thermophilus* HB27 or HB27 Pro- (Koyama et al., *J. Bacteriol.* 166:338–340 (1986)). We reasoned that the introduction of plasmid DNA from related Thermus species, which contained a complete thermophilic ori, would confer plasmid replication within HB27.

The thermophilic eubacterium Thermus species YS45 (Raven et al., *Nucl. Acids Res.* 21:4397 (1993)) contains two cryptic plasmids, and grows between 55° C. and 70° C. These two Thermus plasmids were named pTsp45S and pTsp45L. These plasmids were digested with a variety of restriction endonucleases to produce fragments that can be cloned into pUC19-derived vectors. A pUC19-derived plasmid with a 4.2-kb XbaI fragment of the small plasmid (pTsp45S, 5.8 kb) of YS45 replicated within HB27. Therefore this XbaI fragment must contain a thermophilic ori. Subsequent deletion analysis revealed that only 2.3 kb (an NheI fragment) within the 4.2 kb was necessary for thermophilic plasmid replication, and that it encodes a replication protein (RepT). The repT gene encodes the 341 amino acid protein, RepT, with predicted molecular mass of 38.2 kDa.

A second Thermus plasmid replication origin from pTsp45L was defined within a 9 kb SphI fragment. This fragment encodes a gene (parA) for plasmid replication and partition. It also contains direct repeats of 5' RRCTTTTYYY 3' (SEQ ID NO:1), 5' RRYTTTG 3' (SEQ ID NO:2), and an inverted repeat of

5' TTAACCTTTTTTCAAGAAAAAGAGATAA 3' (SEQ ID NO:3)

3' AATTGGAAAAAGTT CTTTTTCTCTATT 5' (COMPLEMENT OF SEQ ID NO:3)

The direct repeats and inverted repeats are important for pTsp45L plasmid replication. Deletion of these repeats abolished replication activity in Thermus.

BRIEF DESCRIPTION OF THE FIGURES

FIG. 1 is the DNA sequence (SEQ ID NO:4) of repT gene from pTsp45S and its encoded amino acid sequence.

FIG. 2 is the promotor sequence (SEQ ID NO:5) upstream of repT gene.

FIG. 3 is the entire DNA sequence (SEQ ID NO:6) of Thermus plasmid pTsp45S.

FIG. 4 illustrates the genetic organization of Thermus plasmid pTsp45S. The gene repT encodes RepT for plasmid replication.

FIG. 5 is the parA DNA sequence from pTsp45L and the encoded amino acid sequence (SEQ ID NO:7).

FIG. 7 is the entire DNA sequence of Thermus plasmid pTsp45L (SEQ ID NO:8).

DETAILED DESCRIPTION OF THE INVENTION

Figure 6:
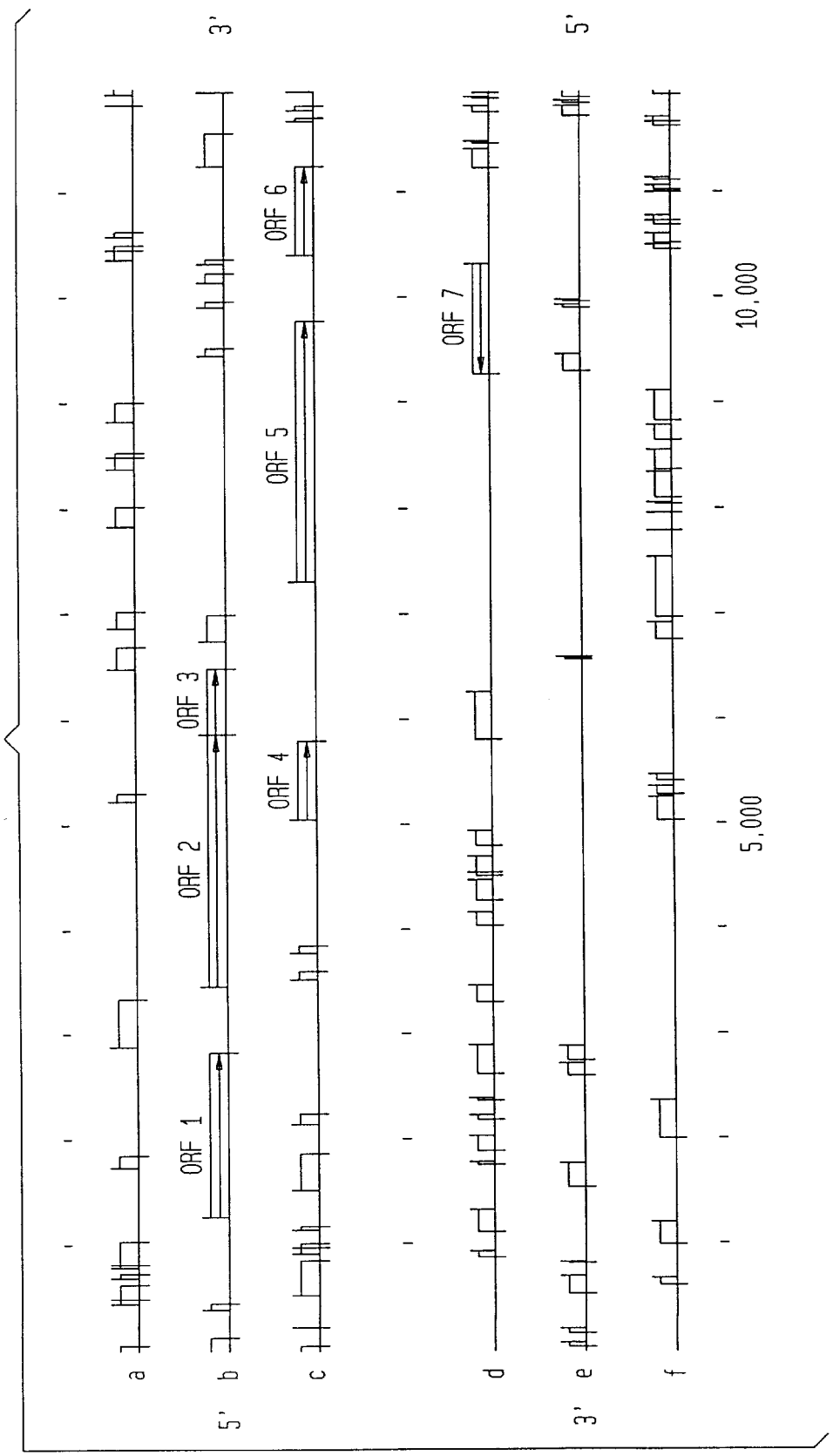
FIG. 6 is the seven open reading frames encoded by pTsp45L. Frames a, b, and c are encoded by the top strand. Frames d, e, and f are encoded by the bottom strand.

The method described herein by which a Thermus plasmid replication origin is preferably cloned and selected comprises the following steps:

1. The plasmid DNA of a target host, such as Thermus species YS45 plasmid pTsp45S and pTsp45L, is purified.
2. The plasmid DNA is digested with appropriate restriction endonucleases; for Thermus species YS45, HindIII, KpnI, PstI, SphI, and XbaI are used to generate 1 to 12 kb restriction fragments. This map is used to orient and localize genes within the plasmid.
3. The digested plasmid DNA is then ligated into similarly cleaved/CIP treated vectors such as pUC-EKR or pUC-EKF ($Ap^R$ at 37° C., $Km^R$ at 50–65° C.) cloning vectors. The ligated DNA is used to transform an appropriate host, e.g., a $HsdR^-$, $McrBC^-$, $Mrr^-$ strain, such as E. coli constrain RR1. The DNA/cell mixtures are then plated on ampicillin selective media to grow only transformed cells to form primary restriction libraries, such as HindIII, KpnI, PstI, SphI, and XbaI DNA libraries for Thermus species YS45.
4. The recombinant plasmids are purified to form the primary plasmid library that might contain thermophilic plasmid origins. Plasmids are digested in vitro with a variety of endonucleases to confirm DNA inserts.
5. The plasmid DNA libraries are used to transform an appropriate thermophilic host cell such as Thermus thermophilus HB27 ($Pro^-$) cells and transformants are selected on Km plates at 60°–65° C. for 48 hours.
6. Individual $Km^R$ transformants are amplified in small culture at 65° C. and plasmid DNA is isolated from the overnight cell culture. The plasmid DNA is then digested with an appropriate restriction endonuclease (e.g., HindIII, KpnI, PstI, SphI, or XbaI) to cut out the Thermus DNA insert.
7. One clone from the XbaI library described above contained a 4.2 kb Thermus DNA which replicates in both Thermus and E. coli. The 4.2 kb insert DNA of the recombinant pUC-EKF clone was sequenced. To facilitate sequencing, the insert DNA was further sub-cloned within pUC19 based upon preliminary sequence and mapping. The sequenced DNA was then assembled to match that of the thermophilic plasmid map. The remaining DNA fragments from pTsp45S were also cloned and sequenced. In this way, the thermophilic plasmid (pTsp45S) was completely sequenced.
8. To reduce the size of the Thermus replication origin, the 4.2 kb XbaI fragment was further digested with restriction enzymes and subcloned into pUC-EKF or pUC-EKR. One recombinant plasmid contained a 2.3 kb NheI fragment that replicates in Thermus and E. coli. This plasmid pUC-EKF-Tsp3 is a Thermus-E. coli shuttle vector.
9. One open reading frame of 1026 bp encoding a 341-amino acid protein was found within the Thermus origin. Deletion of 234 bp (78 amino acid residues) within this gene abolished the Thermus replication function. Insertion of stop codons within this gene causes premature termination and negates the Thermus transformation. Therefore it was determined that this gene (repT) is required for plasmid replication in Thermus HB27 ($Pro^-$) cells.
10. Two Thermus promoters were found upstream of the repT gene that are important for repT expression.
11. Plasmid pTsp45L (a mixture of pTsp45L and pTsp45S) was digested with HindIII, KpnI, PstI, SphI, or XbaI. The digested DNA fragments were cloned into pUC-EKR vector to produce Thermus DNA libraries for subsequent selection of Thermus plasmid replication origin(s).
12. Approximately 450 $Ap^R$ transformants were derived from pUC-EKR +HindIII fragments, +KpnI fragments, +PstI fragments, +SphI fragments, and +XbaI fragments, respectively. pUC-EKR plasmids with HindIII, KpnI, PstI, SphI, or XbaI fragment inserts were amplified in E. coli.
13. The DNA libraries were used to transform Thermus thermophilus HB27 ($Pro^-$). Transformants were plated on Km plates and incubated at 60° C. for two days. Plasmid DNA was extracted from seventeen $Km^R$ transformants and digested with XbaI, PstI, or SphI. Restriction mapping and Southern blot analysis were carried out.
14. The 9 kb SphI Thermus origin insert and the 12 kb Thermus origin insert were from pTsp45L. The entire pTsp45L plasmid can be separated into two SphI fragments, 3 kb and 9 kb respectively. The 9 kb SphI fragment contains the functional Thermus replication origin. The inserts were sequenced by using pUC19 universal forward and reverse primers and by primer walking. Plasmid pTsp45L is 11958 bp, encoding 7 possible genes.
15. Orf3 is most likely the candidate for pTsp45L replication protein, because it has homolgy to RepA protein of Agrobacterium plasmid pTiB6S3, replication protein of Agrobacterium plasmid pRiA4b, plasmid partition protein of Borrelia, partition protein of Frankia, RepA protein of Rhizobium, and DNA partition protein ParA of Caulobacter. Orf2 may be an accessary protein for pTsp45L plasmid replication. Orf3 was renamed as parA gene.
16. There are direct repeats and inverted repeats in the 9 kb SphI fragment containing the functional replication origin. The direct repeats I are:

5' GGCTTTTCTT 3' (SEQ ID NO:9)
5' AACTTTTCCC 3' (SEQ ID NO:10)
5' GACTTTTTTC 3' (SEQ ID NO:11)
consensus 5' RRCTTTTYYY 3' (SEQ ID NO:1)

The direct repeats II are:
5' AACTTTG 3' (SEQ ID NO:12)
5' AGTTTTG 3' (SEQ ID NO:13)
5' GATTTTG 3' (SEQ ID NO:14)
5' RRCTTTG 3' (SEQ ID NO:15)
consensus 5' RRYTTTG 3' (SEQ ID NO:2)

The inverted repeat is:
5' TTAACCTTTTTTCAAGAAAAAGAGATAA 3' (SEQ ID NO:3)
3' AATTGGAAAAAGTT CTTTTTCTCTATT 5'
(COMPLEMENT OF SEQ ID NO:3)
(underlined bases are inverted repeat).

Deletion of these repeats in a HindIII fragment abolished DNA replication in Thermus.

Any Thermus plasmid DNA, Thermus viral DNA, or genomic DNA can be digested with restriction enzymes to generate 2–20 kb fragments. The restriction fragments can be ligated with similarly-cut pUC-EKF or pUC-EKR and transformed into Thermus cells and selected for $Km^R$ transformants. Alternatively, DNA can be extracted from environmental samples, such as water from hot springs and soil sediment from hot springs, digested with restriction enzymes, ligated into similarly-cut pUC-EKF or pUC-EKR and transformed into Thermus cells and selected for Km$^R$ transformants. Because of the small amount of DNA from environmental samples, one can transfer such DNA into *E. coli* first to amplify the DNA library and then transform such DNA into Thermus.

The following Examples are given to illustrate embodiments of the present invention, as it is presently preferred to practice. It will be understood that these Examples are illustrative, and that the invention is not to be considered as restricted thereto except as indicated in the appended claims.

The references cited above and below are herein incorporated by reference.

EXAMPLE I

1. Cloning of a replication origin from a Thermus plasmid pTsp45S native to Thermus species YS45.

Thermus species YS45 (Raven et al., *Nucl. Acids Res.* 21:4397 (1993) obtained from R. A. D. Williams of Queen Mary and Westerfield College, University of London) can be grown in modified *Thermus thermophilus* liquid media (Oshima and Imahori, *J. Sys. Bacteriol.* 24:102–112 (1974)) consisting of 0.5% tryptone (DIFCO Laboratories; Detroit, Mich.), 0.4% yeast extract (DIFCO Laboratories; Detroit, Mich.), 0.2% NaCl at pH 7.5. Cells are plated in this media with 3% agar. Plated colonies are distinguishable after two days incubation at 55°–70° C. Individual colonies form dense liquid overnight cultures (3–10 ml) at 55°–70° C. in a shaking waterbath. One-ml aliquots of overnight cultures are pelleted and stored at −20° C. for up to one month without loss of viability. Overnight cultures are also stably maintained in media with 25% glycerol at −70° C.

Ten ml of 70° C. overnight YS45 culture is diluted 1:1000 in 500 ml of Thermus media, and grown overnight at 70° C. to generate plasmid DNA. Plasmid DNA is prepared via the Qiagen mid-prep protocol (Qiagen, Inc.; Studio City, Calif.) with the addition of 2 mg lysozyme per ml. Lysis is very inefficient without the presence of lysozyme in the first resuspension buffer (Oshima and Imahori, *J. Sys. Bacteriol.* 24:102–112 (1974)). Routinely, between 50–150 µg of plasmid DNA is obtained from 500 ml of overnight YS45 culture.

YS45 contains two plasmids of 5.8 kb (pTsp45S) and approximately 12 kb (pTsp45L) (Wayne and Xu, *Gene* 195:321–328 (1997)). Each plasmid contains a single PstI site useful for linearizing and visualizing the plasmids on agarose gels. Plasmid pTsp45S also contains two XbaI sites that generate 4.2 and 1.6-kb fragments. This plasmid is extensively mapped and cloned into pUC19 as three fragments: 4.2-kb XbaI-XbaI, 0.7-kb XbaI-PstI, and 0.9-kb PstI-XbaI. The 4.2-kb fragment is then further mapped and sub-cloned into pUC19 as six smaller fragments: 0.4-kb XbaI-HindIII, 1.1-kb HindIII-HindIII, 0.7-kb HindIII-HindIII, 0.5-kb HindIII-ScaI, 1.0-kb ScaI-ScaI, and 0.5-kb ScaI-XbaI. Cloning was accomplished by isolating digested fragments from agarose gels and combining them with compatibly cut pUC19 by standard methods (Sambrook et al., 'Molecular Cloning A Laboratory Manual', 2$^{nd}$ ed. (1989)).

The clones are sequenced using universal and reverse M13/pUC primers (New England Biolabs, Inc.; Beverly, Mass.). Preliminary sequencing was used to generate 12 additional primers (synthesized at New England Biolabs, Inc.; Beverly, Mass.) to refine and correct sequencing errors. The primers (shown as top and bottom strand pairs) are:

5'-GGTTCCATAAGGCGGGTCAATATAG-3' (SEQ ID NO:16);

5'-CTATATTGACCCGCCTTATGGAACC-3' (SEQ ID NO:17);

5'-GTGGGGTGGGCTGATCAAGAATCTCCT-3' (SEQ ID NO:18);

5'-AGGAGATTCTTGATCAGCCCACCCCAC-3' (SEQ ID NO:19);

5'-TCACCCACAACCCTCACGCACTCCAA-3' (SEQ ID NO:20);

5'-TTGGAGTGCGTGAGGGTTGTGGGTGA-3' (SEQ ID NO:21);

5'-AGATGTAGTCGTCCAGGGTGAGCCTG-3' (SEQ ID NO:22);

5'-CAGGCTCACCCTGGACGACTACATCT-3' (SEQ ID NO:23);

5'-TTGGTATGTAAAGCCCTTCGCGAGG-3' (SEQ ID NO:24);

5'-CCTCGCGAAGGGCTTTACATACCM-3' (SEQ ID NO:25);

5'-TAGTGGCATCGGTGTTGTCGTGGGT-3' (SEQ ID NO:26); and

5'-ACCCACGACAACACCGATGCCACTA-3' (SEQ ID NO:27)

(underlined bases are in pTsp45s, but were not originally synthesized in these primers).

2. Characteristics of a thermophilic plasmid ori

The 2.3-kb NheI-bounded thermophilic ori is 57% G+C. The 5.8-kb Thermus plasmid pTsp45S is 54% G+C, and there are no other published reports of the G+C content in its natural host, YS45. There are no significant AT-rich regions within the sequenced or.

The thermophilic ori contained one significant ORF of 1026 bp, beginning with GTG and ending with TGA (FIG. 1). The ORF's 341 amino acid could encode a protein with a predicted molecular weight of 38.2 kDa. Centered 10 bp 5' of this ORF is a putative RBS, GGAGG (Hartmann and Erdmann, *J. Bacteriol.*, 171:2933–2941 (1989)). Further upstream, two possible promoter regions (−10 TATTTT, −35, TTGCCA, 17 bp spacing; or −10 TAGGGT, −35 TTGCCC, 18 bp spacing) were found (FIG. 2) with significant homology to the Thermus consensus promoter (Maseda and Hoshino *FEMS Microbiol. Lett.* 128:127–134 (1985)). Database searches (FASTA, BLAST) did not reveal any significant homologies to the predicted protein, or to other possible reading frames.

To test the importance of this ORF in the thermophilic replication, a significant portion of it was deleted. Briefly, pUC-EKF-Tsp3 was digested with NruI+PshAI, removing 234 bp or 78 aa within the ORF. The linearized plasmid was self-ligated, generating pUC-EKF-Tsp3-ΔNP(7.5 kb), then amplified in *E. coli* and used to transform HB27. No pUC-EKF-Tsp3-ΔNP(7.5 kb) Km$^R$ transformants were found. It was concluded that 234 bp deletion within the repT gene abolished the replication function. Similarly, the addition of an XbaI amber stop linker (CTAGTCTAGACTAG (SEQ ID NO:28)) at either the NruI or PshAI site of pUC-EKF-Tsp3 negated thermophilic transformation. This indicated that the repT within the NheI fragment was necessary for replication in the thermophile. We suggest that this ORF of pTsp45S is a novel replication protein (RepT) needed for thermophilic plasmid replication. In addition, analysis of this thermophilic ori revealed two sequences with significant homology to highly conserved DnaA boxes. Although not yet described in Thermus, DnaA boxes are required for binding of a DnaA protein, and for subsequent replication of some plasmids (McMacken, et al., DNA Replication (Chapter 39), pages 586–587 in *Escherichia coli and Salmonella typhimmarium,* American Society for Microbiology, Washington, DC). Both putative DnaA boxes (TTATCACCC (SEQ ID NO:29), TTATCCGAG (SEQ ID NO:30)) of pUC-EKF-Tsp3 lie within the 3' end of repT, and are not within the region deleted in pUC-EKF-Tsp3-ΔNP. Plasmid copy number might be regulated by the relationship between binding of a DnaA homologue at these sites, and transcription of repT A sample of ER2688[pUC-EKF-Tsp3] has been deposited under the terms and conditions of the Budapest Treaty at the American Type Culture Collection on Jun. 22, 1998 and received ATCC Accession No. 98793.

EXAMPLE II

Thermus YS45 strain contains two plasmids of 5.8 kb (pTsp45S) and approximately 12 kb (pTsp45L) (Wayne and Xu, *Gene* 195:321–328 (1997)). Each plasmid contains a single PstI site useful for linearizing and visualizing the plasmids on agarose gels. The two plasmid mixture was digested with HindIII, KpnI, PstI, SphI, or XbaI. The digested DNA fragments were cloned into pUC-EKR vector to produce Thermus DNA libraries and for subsequent selection of Thermus plasmid replication origin(s). Approximately 100, 100, 100, 100, and 50 $Ap^R$ transformants were derived from pUC-EKR +HindIII fragments, +KpnI fragments, +PstI fragments, +SphI fragments, and +XbaI fragments, respectively. Plasmids pUC-EKR with HindIII, KpnI, PstI, SphI, or XbaI fragment inserts were amplified in *E. coli* and the DNA libraries were used to transform *Thermus thermophilus* HB27 (Pro⁻). Transformants were plated on Km plates and incubated at 60° C. for two days. Plasmid DNA was extracted from seventeen $Km^R$ transformants and digested with XbaI, PstI, or SphI. Restriction mapping and Southern blot analysis indicated that the 4.2 kb XbaI fragment Thermus origin insert was from pTsp45S, the 9 kb SphI Thermus origin insert and the 12 kb Thermus origin insert were from pTsp45L. It was concluded that the entire pTsp45L plasmid can be separated into two SphI fragments, 3 kb and 9 kb respectively. The 9 kb SphI fragment contains the functional Thermus replication origin. The two SphI fragments were sequenced by subcloning of one BamHI fragment (1.4 kb), one HindIII fragment (1.9 kb), one SphI fragment (3 kb), two KpnI fragments (2.5 kb, 0.6 kb), three SacI fragments (4.3 kb, 1.9 kb, 1.3 kb), and multiple SmaI fragments into pUC19. The inserts were sequenced by using pUC19 universal forward and reverse primers and by primer walking. Plasmid pTsp45L is 11958 bp, encoding 7 possible genes. These seven genes are named orf1 through orf7 (FIG. 6). Orf1 amino acid sequence has weak similarity to transposases. Orf3 amino acid sequence has similarity to DNA replication protein RepA and DNA partition protein ParA. Orf4 amino acid sequence has similarity to serine carboxy peptidase III. Orf5 amino acid sequence has similarity to UvrB protein. Orf2, orf6, and orf7 amino acid sequences have no homologs to proteins in Genbank. The 3 kb SphI fragment contains orf5 C-terminus portion, orf6 and orf7. Deletion of this 3 kb did not affect pTsp45L plasmid origin of replication. It was concluded that orfs 5, 6, and 7 are not required for plasmid replication. The 9 kb SphI fragment contains the functional replication origin, which contains orf1, 2, 3, 4 and a portion of orf5. Orf1 and orf4 have homology to transposases and proteases, respectively. It was concluded that orf1 and orf4 are unlikely involved in DNA replication and that orf3 is most likely the candidate for pTsp45L replication protein, because it has homolgy to RepA protein of Agrobacterium plasmid pTiB6S3, replication protein of Agrobacterium plasmid pRiA4b, plasmid partition protein of Borrelia, partition protein of Frankia, RepA protein of Rhizobium, and DNA partition protein ParA of Caulobacter. Orf2 may be an accessary protein for pTsp45L plasmid replication. Orf3 (coordinate 5876 to 6478) was renamed as parA gene. The DNA sequence and amino acid sequence of parA is shown in FIG. 5. The location, direction, and organization of the seven open reading frames in pTsp45L are shown in FIG. 6.

There are direct repeats and inverted repeats in the 9 kb SphI fragment containing the functional replication origin. The direct repeats I are:

5' GGCTTTTCTT 3' (SEQ ID NO:9)

5' AACTTTTCCC 3' (SEQ ID NO:10)

5' CACTTTTTTC 3' (SEQ ID NO:11)

consensus 5' RRCTTTTYYY 3' (SEQ ID NO:1)

The direct repeats II are:

5' AACTTTG 3' (SEQ ID NO:12)

5' AGTTTTG 3' (SEQ ID NO:13)

5' GATTTTG 3' :(SEQ ID NO:14)

5' AACTTTG 3' (SEQ ID NO:15)

consensus 5' RRYTTTG 3' :(SEQ ID NO:2)

The inverted repeat is:

5' TTAACCTTTTTTCAAAGAAAAAGAGATAA 3' (SEQ ID NO:3)

3' AATGGAAAAAAGTT CTTTTTCTCTATT 5' (COMPLEMENT OF SEQ ID NO:3)

(underlined bases are inverted repeats).

The repeats and inverted repeats are important for pTsp45L origin of replication, because deletion of these repeats in a HindIII fragment abolished DNA replication in Thermus. The DNA sequence of pTsp45L is shown in FIG. 7. The *Thermus-E. coli* shuttle vector containing pTsp45L DNA replication origin was named as pUC-EKR-Tsp45L9Kb.

A sample of ER2688[pUC-EKR-Tsp45L9kb] has been deposited under the terms and conditions of the Budapest Treaty at the American Type Culture Collection on Jun. 22, 1998, and received ATCC Accession No. 98794.

EXAMPLE III

Thermus strain YS45 (Raven, et al., *Nucl. Acids Res.* 21:4397 (1993) obtained from R. A. D. Williams of Queen Mary and Westerfield College, University of London) also harbors a plasmid. Plasmid DNA was extracted from Thermus species YS45 by midi Qiagen column. The plasmid DNA was cleaved with HindIII, KpnI, PstI, SphI, or XbaI. The digested DNA fragments were cloned into pUC-EKR vector to produce Thermus DNA libraries and for subsequent selection of Thermus plasmid replication origin(s). Approximately 50 to 300 $Ap^R$ *E. coli* transformants were derived from pUC-EKR +HindIII fragments, +KpnI fragments, +PstI fragments, +SphI fragments, and +XbaI fragments, respectively. Plasmids pUC-EKR with HindIII, KpnI, PstI, SphI, and XbaI fragment inserts were amplified in *E. coil* and the DNA libraries were used to transform *Thermus thermophilus* HB27 (Pro⁻). Transformants were plated on Km plates and incubated at 60° C. for two days. Thermus transformants were found in HindIII and PstI DNA libraries. Plasmid DNA was extracted from seventeen $Km^R$ Thermus transformants and digested with HindIII or PstI. It was found that the functional Tse plasmid replication origin was contained in a ~7 kb HindIII or PstI fragment. The shuttle vector was named pUC-EKR-Tse7 Kb.

EXAMPLE IV

Thermus cells can be grown in modified *Thermus thermophilus* liquid media (Oshima and Imahori, *J. Sys. Bacteriol.* 24:102–112 (1974)) consisting of 0.5% tryptone (DIFCO Laboratories; Detroit, Mich.), 0.4% yeast extract (DIFCO Laboratories; Detroit, Mich.), 0.2% NaCl at pH 7.5. Thermus cells can also be cultured in 4 to 10-fold diluted rich both at 50°–75° C. Ten ml of overnight cell culture is diluted 1:1000 in 500 ml of Thermus media, and grown overnight at 50°–75° C. to generate plasmid DNA. Plasmid DNA can be prepared via the Qiagen MIDI/MAXI-PREP protocol (Qiagen, Inc.; Studi City, Calif.) with the addition of 2 mg lysozyme per ml or any other plasmid preparation method such as alkaline lysis or boiling methods. The purified plasmid DNA can be digested with restriction enzymes to produce DNA fragments of 2 to 20 kb. The plasmid DNA can also be sonicated to produce blunt end framgents and be made into sticky ends by addition of deoxynucleotides by terminal nucleotide transferase. The DNA fragments can be cloned into pUC-EKF or pUC19-EKR and the ligated DNA can be used for thermophilic transformation into Thermus cells. Transformants can be selected by plating cells on Km plates. Any $Km^R$ transformants should contain Thermus plasmid replication origins. The origin can be further subcloned and sequenced. A minimal replication origin can be defined by subcloning smaller DNA fragments into pUC-EKF or pUC19-EKR and the resulting plasmid DNA can be used for thermophilic transformation.

Alternatively, plasmid DNA, Thermus viral DNA or genomic DNA can be extracted from environmental samples such as water from hot springs and soil sediment from hot springs and digested with restriction enzymes and ligated into similarly-cut pUC-EKF or pUC-EKR. The ligated DNA can be transformed into Thermus cells and select for $Km^R$ transformants. Because of the small amount of DNA from environment samples, one can transfer DNA into *E. coli* first to amplify DNA library and then transform into Thermus. The thermophilic replication origin can be further subcloned and sequenced. A minimal replication origin can defined by subcloning smaller DNA fragments into pUC-EKF or pUC19-EKR and the resulting plasmid DNA can be used for thermophilic transformation.

What is claimed is:

1. A method for cloning Thermus sp. plasmid genes comprising the steps of:
   (a) isolating plasmid DNA from Thermus sp. cells wherein the plasmid comprises at least one Thermus sp. origin of replication;
   (b) inserting said plasmid DNA into a recombinant plasmid comprising a thermostable kanarnycin-resistance gene and an *E. coli* replication origin to produce a cloned recombinant plasmid;
   (c) transforming an *E. coli* sp. host cell with the cloned recombinant plasmid of step (b) and culturing said *E. coli* sp. host cell for the expression of said cloned recombinant plasmid;
   (d) isolating the cloned recombinant plasmid from said cell; and
   (e) transforming a Thermus sp. host cell with said cloned recombinant plasmid from step (d) and culturing said Thermus sp. host cell.

* * * * *

UNITED STATES PATENT AND TRADEMARK OFFICE
CERTIFICATE OF CORRECTION

PATENT NO. : 6,207,377 B1
DATED : March 27, 2001
INVENTOR(S) : Jay Wayne and Shuang-yong Xu It is certified that error appears in the above-identified patent and that said Letters Patent is hereby corrected as shown below:

Column 2,
Line 36, replace "TTAACCTTTTTTC" with-- TTAACCTTTTTTC --
Line 38, replace "CTTTTTCTCTATT" with -- CTTTTTCTCTATT --

Column 3,
Line 14, replace "constrain" with -- strain --

Column 4,
Line 48, replace "RRCTTTG" with -- AACTTTG --
Line 51, replace "TTAACCTTTTTTC" with -- TTAACCTTTTTTC --
Line 53, replace "CTTTTTCTCTATT" with -- CTTTTTCTCTATT --

Column 6,
Line 3, replace "GTGGGGTG" with -- GTGGGGTG --
Line 5, replace "CCCACCCCAC" with -- CCCACCCCAC --
Line 17, replace "ATACCM" with -- ATACCAA --
Line 32, replace "or" with -- ori --

Column 8,
Line 15, replace "CACTTTTTTC" with -- GACTTTTTTC --
Line 24, replace "TTAACCTTTTTTCAAAG" with -- TTAACCTTTTTTCAAG --
Line 26, replace "AATGGAAAAAGTTCTTTTCTCTATT" with --
AATTGGAAAAAGTTCTTTTTCTCTATT --

Column 9,
Line 12, replace "MIDI/MAXI - PREP" with -- midi/maxi - prep --

UNITED STATES PATENT AND TRADEMARK OFFICE
CERTIFICATE OF CORRECTION

PATENT NO.    : 6,207,377 B1
DATED         : March 27, 2001
INVENTOR(S)   : Jay Wayne and Shuang-yong Xu It is certified that error appears in the above-identified patent and that said Letters Patent is hereby corrected as shown below:

Column 35,
Line 8, replace "kanarnycin" with -- kanamycin --

Signed and Sealed this

Ninth Day of October, 2001

*Attest:*

NICHOLAS P. GODICI
*Attesting Officer*   *Acting Director of the United States Patent and Trademark Office*

SEQUENCE LISTING

```
<160> NUMBER OF SEQ ID NOS: 30

<210> SEQ ID NO 1
<211> LENGTH: 10
<212> TYPE: DNA
<213> ORGANISM: Thermus sp.

<400> SEQUENCE: 1 rrcttttyyy                                                           10

<210> SEQ ID NO 2
<211> LENGTH: 7
<212> TYPE: DNA
<213> ORGANISM: Thermus sp.

<400> SEQUENCE: 2 rrytttg                                                               7

<210> SEQ ID NO 3
<211> LENGTH: 28
<212> TYPE: DNA
<213> ORGANISM: Thermus sp.

<400> SEQUENCE: 3
ttaacctttt ttcaagaaaa agagataa                                       28

<210> SEQ ID NO 4
<211> LENGTH: 1026
<212> TYPE: DNA
<213> ORGANISM: Thermus sp.
<220> FEATURE:
<221> NAME/KEY: CDS
<222> LOCATION: (1)..(1023)

<400> SEQUENCE: 4 gtg aag aac gaa aaa acc ttc ttt gaa gag ctt tac gag gct tta gag    48
Met Lys Asn Glu Lys Thr Phe Phe Glu Glu Leu Tyr Glu Ala Leu Glu
  1               5                  10                  15
```

```
gaa acc cac gac aac acc gat gcc act agg ggg tca gat agg ggg tca        96
Glu Thr His Asp Asn Thr Asp Ala Thr Arg Gly Ser Asp Arg Gly Ser
             20                  25                  30 gag gac ttc ttc ttg gcc acc gac ccc cct cca gat gga ggt gcc gaa       144
Glu Asp Phe Phe Leu Ala Thr Asp Pro Pro Pro Asp Gly Gly Ala Glu
     35                  40                  45 aat cgc ctc gcg aag ggc ttt aca tac caa aaa gag gca ctt agg att       192
Asn Arg Leu Ala Lys Gly Phe Thr Tyr Gln Lys Glu Ala Leu Arg Ile
 50                  55                  60 gct tta ccc gag aaa gac cat gag gct ttc ctt tcc tct gtt ggg gcc       240
Ala Leu Pro Glu Lys Asp His Glu Ala Phe Leu Ser Ser Val Gly Ala
 65                  70                  75                  80 ccc cct ata cca cca gct gaa ccc ccc gtt ggg aat gta tgt caa gcc       288
Pro Pro Ile Pro Pro Ala Glu Pro Pro Val Gly Asn Val Cys Gln Ala
                 85                  90                  95 gtc cag gac ggg cct cag aag ctt ctg gaa ctc ctc cag gag att gcc       336
Val Gln Asp Gly Pro Gln Lys Leu Leu Glu Leu Leu Gln Glu Ile Ala
            100                 105                 110 cgc tcc acc atc ccc tac ggc aac cgg gag ctc tgg agg aag gtg ggg       384
Arg Ser Thr Ile Pro Tyr Gly Asn Arg Glu Leu Trp Arg Lys Val Gly
        115                 120                 125 acg gtc gtc ttc atg gtc ccc ctg gag atg ttg gcc ctc aac ctg ggg       432
Thr Val Val Phe Met Val Pro Leu Glu Met Leu Ala Leu Asn Leu Gly
    130                 135                 140 gtc acc cgg cag acc gtc cac gcc tgg aag aag gtc ctt gag aaa aag       480
Val Thr Arg Gln Thr Val His Ala Trp Lys Lys Val Leu Glu Lys Lys
145                 150                 155                 160 ggc ctg gtg gcc acc gac gtc ctt cac caa acc gtc aac ggg gag cgc       528
Gly Leu Val Ala Thr Asp Val Leu His Gln Thr Val Asn Gly Glu Arg
                165                 170                 175 cgg gcc atc ggc acc ctt tgg gcc gtc cgg ctg agg cca ggg aaa gcc       576
Arg Ala Ile Gly Thr Leu Trp Ala Val Arg Leu Arg Pro Gly Lys Ala
            180                 185                 190 agg ctc acc ctg gac gac tac atc tac ccc tgg agg aac ctc gcc cta       624
Arg Leu Thr Leu Asp Asp Tyr Ile Tyr Pro Trp Arg Asn Leu Ala Leu
        195                 200                 205 gac atg gcc aac ggc gtg ctc tcc ttc aac tgg gtc aag gcc tac cag       672
Asp Met Ala Asn Gly Val Leu Ser Phe Asn Trp Val Lys Ala Tyr Gln
    210                 215                 220 gac cac gga atc cgc ccc acc ctg gac gtg ctg gtc ctc tgg gct cag       720
Asp His Gly Ile Arg Pro Thr Leu Asp Val Leu Val Leu Trp Ala Gln
225                 230                 235                 240 ggg aaa agg gtg atg ccc aac acc aag acc gtg gcc gtt gac ctg ggc       768
Gly Lys Arg Val Met Pro Asn Thr Lys Thr Val Ala Val Asp Leu Gly
                245                 250                 255 ctc atc ctg gtc ctc ccc gag gtg gag cgt tcc aaa ctc ccg gcc ctt       816
Leu Ile Leu Val Leu Pro Glu Val Glu Arg Ser Lys Leu Pro Ala Leu
            260                 265                 270 atc acc ctc att gct acg tac att gcc gat ctc cta gat gac cgt cgt       864
Ile Thr Leu Ile Ala Thr Tyr Ile Ala Asp Leu Leu Asp Asp Arg Arg
        275                 280                 285 tca aga cgt ttc tat gca ggc ttg ctg tgg gct gtg gcc agg ggt gaa       912
Ser Arg Arg Phe Tyr Ala Gly Leu Leu Trp Ala Val Ala Arg Gly Glu
    290                 295                 300 ctc ccc gcg caa tat cta ttt gcc gtc cta atg cgg gtt atc cga gat       960
Leu Pro Ala Gln Tyr Leu Phe Ala Val Leu Met Arg Val Ile Arg Asp
305                 310                 315                 320 tac acg gat ggc cat ctg aca cga ccg gga gcg tac cta gtg aag acc      1008
Tyr Thr Asp Gly His Leu Thr Arg Pro Gly Ala Tyr Leu Val Lys Thr
                325                 330                 335
```

```
ctc aag gag gcc tcc tga                                                  1026
Leu Lys Glu Ala Ser
        340

<210> SEQ ID NO 5
<211> LENGTH: 180
<212> TYPE: DNA
<213> ORGANISM: Thermus sp.

<400> SEQUENCE: 5
ctataacggc cttttaggag gggggattgc cagccgctgg gctgacggtt attttggacc         60
cataaaaagg cgaaaccgag gcggttgccc cggatcaccc ccaagaccta gggtaacgcc       120
tcgggctcca gatgacaagg aggtccgagg gtgaagaacg aaaaaacctt ctttgaagag       180

<210> SEQ ID NO 6
<211> LENGTH: 5849
<212> TYPE: DNA
<213> ORGANISM: Thermus sp.

<400> SEQUENCE: 6
tctagaaggt cagggtggac aaggaaaaca ccatagcccc tgccaagaag atggacgagt        60
tggtgtccgg aaaagtggcc atccggggcg ctcttgacaa ctattttcca gcggtggcca       120
ccggcattgg ccacgaggta cgagcttgtg gagtagacgc ccacaaaggg gtcgtcctca       180
aacttctttt ctagtgccgc ttggacgaag gggaggaaga ggaaaggctt catggcctca       240
cctccttccc ctcctccttg gcggcttag cggcgtaaaa ctctgagacg gcctgaagtt       300
tagggatttc gctttcgggg ataagaatcc ggcggctcag gggatgccgg atggccctta       360
tcctgccgtc ccttatgtac tcgtaaatgg tggccttggg tactttaaac cgttctgaaa       420
cttctctaac agagagcaca aaacctctaa aaacctatca atcccaccga ttccagtata       480
ccataaatgg cacaaagttt tgagaaggtg gtcaaacaaa aaggctttct cggtcaggtt       540
atggtgaggt gggggcggtc aaaggccgac ttaagtttgg taaagccggg aggaagcaaa       600
ccggggtgtt accatgcaac agatggccga gtggaacgtg tggacacaga gaagcgttga       660
gcttctggag aagggg tatt tggataaact actgcaggtc tataaagggg aaagtggctc       720
ttcgaggtca gtaccagagg aggtagagga aaaacttcgc gaggcctaca aggcatacga       780
ggggaggcag gatagtccgg aggcagaaac gaaactcgtg gaagccgtgc taaatgccag       840 aaaaaggtc gagcggtccc ccttcaatca cccctacctg cctttggtct actacctggt       900
ttcggaaaaa gcagaaaaag cgaacaaggc ccttgaggag gcattgcagg aggttgcctc       960
aaagcaccca gaaccatcc gcgtcctggc aaggaagcg caaagaagag gcgtagaagc      1020
cttgatccaa aggctcaagg agcctcccga aataaatcgg cagatagggc cgatgttcaa      1080 aagtggtac aaagaagagc taagggggaa aatagaagag aggcttccag gccctaccaa      1140
accaaagatt gtggtagtat cccctgaaaa aagtaaaccg gagcaagcac cccttattgc      1200
ggagagagaa gcgggcatca tcatatacac gggatcggat gaagctttga agatgccgc      1260 caaggaaaac ctgggccttg gcgaggaagc agaactaggc accaagggcg tagatttcta      1320
cgtggtcatc cggcgtagcc ctgaagagac atggcaccta acaggagaag tgaagtttca      1380
atccgacttt ggcggaaacc aagacaacca gaaactagta gcaaaggctt ccataaggtt      1440
ggaccttgag aagaggcaca taggaatagt ggtggtggac ggaatgcctg tggtgagcaa      1500
gtttcgtggg tgggccggac tggggaaaga acgatcgtt acatccgtac tcctccttcc      1560
agacctgata gcggagctct accaaaaggg tgaagaagcc ctgggcctct agaaggcgga      1620
```

```
cacaatctca aacttgtgct gtagcctggg gaaatcctct aacacccttc tagtgaaggc    1680
tttgaccgcc tcccaggagg catctatgcc gatggatcgc cgctttaaga ggggtgaggc    1740
tataagcgta gtaccggagc ctgcgaaggg atcgagcact aaatccccct cgttactccc    1800
tgtttggacg atgagcttga gcatgtccag atttttctcg gtggggtatc gcgggtacgg    1860
aggatccttg aactgccaaa cgtcctggag cttcttcccc ttcttcaggc gatcccgagc    1920
gtaaactttc ttccgcggca ccccgttctt tgaccagaca ataagccctt gagcgtctag    1980
ctcgtcaagc ttctccgggg gatagcgcca atgccgtcca ggaggggaa gtattcctcg     2040 ccaaggcctt ccggtagggc catccttggt ttctccagga gcatgcaggg gattggtggt    2100
gtaccgttcc ccgttctcgt ctacaaaggg aaaagccta gcgatctcct cttccgaata     2160
ggggctagcc gattcgttcc aaacgtagtc ccgcgttttg gagtagacga ggatcatgtc    2220
cttttgcgat ccgaaggcct tacgggaaaa gttttggga tttgaagcga tgcgggcgat     2280
atggttaacg aagtttcgcc ggccaaagac ctcatcaagg atgagcttca cctcgaaccc    2340
gtatttctcg tctatgtgaa cgaagatcag tcctgagtcc gccatcagct ccctgagaag    2400
tatcaagcgc tccctcagga actccacaaa ctgaggacca tcgagggtgt catcgtagcc    2460
caactgaccg ttttgggct ggctgacggt agcaacgcga tctgtttcat cgccgccaac     2520
gagaaactgc tggccggttc cataaggcgg gtcaatatag accaactgga ccttccccgc    2580
atacccacca ggctcccgga gcatccaccg gagaacctga ccgttttccc ccaaaaagta    2640
ggtgccaata ggatcaatct caaaaggggg gcatttccc cctaggaaga ggagggtttc     2700
ttttcgcaaa acaagttgtg gggtgggctg atcaagaatc tccttctcat cgcgttttcc    2760
ggggtagacc aacctaaagg gcgaaggttc cgaggttttc gaggctttca aggggcttt     2820 tcgggtcaaa ccagggtagc tacggctcat tcttccctcc ccacagcgct cttaagcagg    2880
acctcatcac ccacaaccct cacgcactcc aaccaaggaa tccgccaaag gcggcctacc    2940
ttttgagccc gtatcttccc ctgacgtata gaccttcgga tcgtctcagg gtgcacccga    3000
aggatgtctg caagctcctc gggggtcagg tacacgggct tcatcctcat gacacaacct    3060 tacccccacag aggacaacac atgcaactat gggcaaagta gacaacgaga ccaaaagctt    3120
gggccactct ctcaggaggc ctccttgagg gtcttcacta ggtacgctcc cggtcgtgtc    3180
agatggccat ccgtgtaatc tcggataacc cgcattagga cggcaaatag atattgcgcg    3240
gggagttcac ccctggccac agcccacagc aagcctgcat agaaacgtct tgaacgacgg    3300
tcatctagga gatcggcaat gtacgtagca atgagggtga taagggccgg gagtttggaa    3360
cgctccacct cggggaggac caggatgagg cccaggtcaa cggccacggt cttggtgttg    3420
ggcatcaccc ttttcccctg agcccagagg accagcacgt ccagggtggg gcggattccg    3480
tggtcctggt aggccttgac ccagttgaag gagagcacgc cgttggccat gtctagggcg    3540
aggttcctcc agggggtagat gtagtcgtcc agggtgagcc tggctttccc tggcctcagc    3600
cggacggccc aaagggtgcc gatggccccgg cgctccccgt tgacggtttg gtgaaggacg    3660
tcggtggcca ccaggcccttt tttctcaagg accttcttcc aggcgtggac ggtctgccgg    3720
gtgaccccca ggttgagggc caacatctcc agggggacca tgaagacgac cgtcccacc     3780 ttcctccaga gctcccggtt gccgtagggg atggtggagc gggcaatctc ctggaggagt    3840
tccagaagct tctgaggccc gtcctggacg gcttgacata cattcccaac gggggttca    3900 gctggtggta taggggggc cccaacagag gaaaggaaag cctcatggtc tttctcgggt    3960
aaagcaatcc taagtgcctc ttttggtat gtaaagccct tcgcgaggcg attttcggca    4020
```

-continued

```
cctccatctg gagggggtc ggtggccaag aagaagtcct ctgacccct atctgacccc      4080 ctagtggcat cggtgttgtc gtgggtttcc tctaaagcct cgtaaagctc ttcaaagaag      4140
gttttttcgt tcttcaccct cggacctcct tgtcatctgg agcccgaggc gttaccctag      4200
gtcttggggg tgatccgggg caaccgcctc ggtttcgcct ttttatgggt ccaaaataac      4260
cgtcagccca gcggctggca atcccccctc ctaaaaggcc gttataggcc ctgctaggag      4320 ggggtagta ctttcctacc ccctaggct tggagaggcc ttaggaggtc tcctagggcc      4380
tcgtgggggt gtaggggtaa cctcatggcc aggccgccg gctcgggact ctggaggagg      4440
cctccatagc ctactcgtgg tggaggtttg tgaagggggtt cactaatgca tacggctagc      4500
ctcgggatca cggccaaatg gtatgcaggt tttggtataa aaccctcagg tttgaggcta      4560
gtttatgtcg gttttatgca cctttgactc ggatcacggg cataaacacc agtttcctgc      4620
acgaaagaaa actttcgcga tctaagaggg gaaagaggt gtagagggac ggccttcatg      4680
aaagttggcc tcttaggagg ccgttgtaga gggccgtctc gggttcaaat cctttccctc      4740
tctctccagg tttccgaggt tcgaggtctt ggtccaggtc ttgtaccaag ttttttgacca      4800 aagtctattc tcggaatata ggggtatctt gtctatcttc cctacgggat atctctgtct      4860
gtgtgaactt gatcccatcc caatacatat ctcaatctcc taatctcctc ttctctccag      4920
atccctaatc tcttcttcta cctctttctc ctcccaatta agaatggaga ggaaaaaccc      4980
cgaccagaac gagcttctcg gggtcagttt cggtaatctc gggacaggtt ttcatcgtct      5040
aggacgagga ttagggcatg aaaaatgggc tttgacaaaa tctttctaaa aaatactccc      5100
cgaggttggg gaagtgccct cggggagaag attttttggca gtttagatgt tatgctctat      5160
cacgggccgg aggcctccac gataagttgt cttggccaag taccgggcca ggtcggggggt      5220 gctcttcagc gtggtgatgg tactttcacg gaagttcaca agtcctttta gaggcttcag      5280
gtcggggata gtgctcaagt actcccaagc gttctcgggc ccgtggtcgg ggagaaggac      5340 aaagggggtcg ggcaaaagtt catctttgta cttaggacgg attactttag cacctgataa      5400
cttcagggcc gttaagaagg gcctcacctc ggagacgggt ggaaggagga cgtgggcgtg      5460
gaagaagacg aacccccgatt tttgggaagt ctccctccag tttgatgatg aacgttggga      5520
ggaagccggc caggatgtct ttcatcgcgc ctcgaacctc ggacacataa aaaactttcg      5580 tgttttgtcag ggcaagagtg ctatgtatga ggtaaccttc gggagtacaa agtgcctcaa      5640
gccgcctttc ccaacgctcc aaaactctag ggtcaggtgg tttaggtttt ctgaaaaact      5700
ctagcttttc agtggtcatt cctcaccct ctagcacgta ctctggaagg taaacctttg      5760
acacagcggc caagtctagc gtctcccagt ccagttggtc tgggacgcgt gagaagggga      5820
ggggcttggt gtagaggacc agaagaccc                                        5849
```

<210> SEQ ID NO 7
<211> LENGTH: 603
<212> TYPE: DNA
<213> ORGANISM: Thermus sp.

<400> SEQUENCE: 7

```
atgatcgtgg ctgtcaccgg cttcaaggga ggggtgggga agaccaccac ggcggtccac       60
ctggcctgct tcctggccga gcggggcccc accctgctgg tggacgggga ccccaaccgc      120
tccgccacgg ggtggcaccg gaggggaggc ctccgggtga ccgtggtgga cgagcgggtg      180
gcggcccggt acgcccggga gcacgcccac gtggtcatag acacccaggc cgccccacg      240 gaagaggacc tccgggccct cgccaagggg gtggacctgc tggtcctgcc cacgtccccc      300
```

```
gacgccctgg ccctggaggc cctcctggcc accctggaag ccctgcgggg ggcggaggcc    360
cgcttccggg tcctcctgac catggtgccc ccgcccccga gccgggacgg ggaggaggcc    420
cgggccctct tggggggcgga gggcgttccc ctcttcacag gctgggtgag gcgggcggca    480
gccttcccca aggccgccct cctgggggtg cctgtctacc gggtgcccga ccccagggcg    540
aggctggcct gggggggacta cgcgcgggtg ggggaagagc tcctgaagga ggtgggggga    600
tga                                                                  603

<210> SEQ ID NO 8
<211> LENGTH: 11958
<212> TYPE: DNA
<213> ORGANISM: Thermus sp.

<400> SEQUENCE: 8
cttatacaca caaactatac acgtctctat cgggcttttc ttagcgccat gtaaaacacc     60
cctcccatct ccgggtgttt acagcggata cgggaggttc agcgggaact tttccccttg    120
ttgaaacttt ggggtctgag gctcaacagc agaacagctt aggttgactc aacacagctc    180
ataagtccct tcattatcgc ctgagtcaac ctatgagtta acctttttc aagaaaaaga    240 gataagtgag ttttgtcctc tagcacgact tttttctttg agtcaacctc tgtgccgacc    300
cccccgattt tgagtcaacc ccctttgag ccgaaacttt gttggcacag gggttgactc    360
aggggttgac tcaacgcgaa tggcctctgg aagggcgttg agccgacccc tccctcgtgt    420
gccgaccccc gctccactat gagcaggggg gaaagttacg ggaaaagttc cccaagtccc    480
ccttgacaaa agatgacaat cgagttaatg tcacagcgat gcgtcactca cctctggctg    540
ggctcaccca gatgcgtgcg cgaacgtttc agagcctcct tcgattcctg gccagggagg    600
ggcgctaccc cactggtgta gagctcgcca aggtgctggg gcgcagcccg cacgccacgt    660
gggccatgct cagggctttg acccgtcatg gactcgtgga acggcacgag ggggtctatg    720
ttctgacccc tgcgggcgta gaacttgcca ggaccctggg aaccaccgtg tggcgtgggg    780
atgaggaggt acagacggcg ttacagctgc taggagtcgg tcatgccgcc gaggacaggc    840
gctgaagctt ttgagccggg gccctcaccc aaggccaccc cggctcctct cccctgggat    900
cccaaatgga tccctcagcg ccattatcct cctggcggtc ctatagcgca aggaggtagt    960
ggtgacgaaa cacacaaatg tttcaccca cctttggat gccgtagagg agctcgctcg   1020
ccagattgct gaaaccgcta acaaggctta ttccagccat ttcaggcaga ttgtcaaagt   1080
cctgccgcct gaggttcccg acctctacgc ctggctggcc gccctggatg actccgccat   1140
cgaggagctt gccccagcgcc tgagggaggt cgagggaagc cccgccccc atttcaccgc   1200 cgccctcaaa aaggccctgg ccatcgccct acagcggcgg accctcgccg agatgccccc   1260
cacgttcgcc aacgcgctcc gctgggcgat ggaacggcaa ggggtgagca tccgcaagct   1320
tgcgagagag gtagggggtca gcaaaaccac tgttaaaaag tggcgtggag gccgctttgt   1380
ccctcgttca cggacctacg tgaggaggtt ggaggagatc ctggacctcc cggaaggcgc   1440
cctttcggga cgactacccc gctgggggtt gccaaaaata ttggaaggtg ttgaggggaa   1500
agatgcccct tatcccgggt tcacgcggac cttcctgcgc gtggccgccc tggcgcgcta   1560
cggccgcccg tgggatgatc tctctcccga cgaacaggag gcccttcggc gcgaggacga   1620
agaccggtgg acccgcctct ccaaccgcca gaagcgagtg cgaaaggcca gtcaaaaacc   1680 tttttcggctt tcctttgacg agtggccaac tgaggctcgc aaagaatggg aggactacga   1740
gcgctatgcc tcatcggcac ctgggagcat cgcgcgcgtg caggcggcgc ttgcgggcgc   1800
```

-continued

```
acctctcgct cccacgaccg tgcggacgga aacgctcgag cgtgagcgga tacttataga   1860
actgttctac ggctactgtg taaacgaacg gggcctcgac agcaacgcgt tgagcctcgc   1920
cctcctcaca gacctggagc tcgtccaatc gtacctggag tggcgcgtga ataggtacaa   1980
ggacgaggat ttaccccccg ttactcgatc ggaatacatg tttatcgccc tggtgaaaaa   2040
actccacaga ggttatctcc gcgcccttgg gcttgggta gacccggacg gggtgaaaga   2100
gctggaacgg aaactgaaaa tcgccggaat tgatgtcacg gacggctacc acgcggtgga   2160
gcccctcctg gaaactcacg agcccctccg ctgggtgctg gatggcatcc ggctcatgct   2220
ccgcgatgcg gcggggcggg taggcaacct gctgacaccc caaatcccca ccgccaaaag   2280
cgaagcgggc gaagcgttcg ccctctaccg ggacgtcgtt ctgctttgga tgatggtggg   2340 ccacccctc cgggcgaagc attactacga agctcgcttg gacatgagcc agttccaaga   2400
cggggatttc gctcccgggc ggggacacgt ggggcgggcc ggcggagggt actacctggc   2460
ctaccgcaaa gtggagttca aaaacgcccg aggccaggtc tttcagagcc tccaggacca   2520
cgatctcgtc acgttccccc tggacgaccc cgagcaccct gtcctggtcc tggacgtgaa   2580
cgggatgcgg tactccctca acgagctctt tcacgtctac ctgcgcacga tcctctcccg   2640
cctggcccag gcctgggccg gaccggtccc ctcctgcccc tgtttccggg tgccgatacg   2700
aggctcagac ttgcgcacat cgttcgcagg gcgcgccgcct acgtggccgc cgtgcccggg   2760
gtaccccaga aacttttgcc cttcggcccc cactccatcc gccacgtggt ggccacggag   2820
gtcgtgaagc gcacgggctc ttttgaggcc gccgccaacg tgctcctgga tagcatagac   2880
atggtcgttc gacattacgc ccgttcgttc cccgcgaccg taacagtcac ggttggcggg   2940
ctaacgcccg cgcccgggga ggtgagcggt gagggacctc cacgactttt tcctggcccg   3000
ggtggacgaa ctggtgccgg aactcctacc cggggcgcgg cgggtgggcg acgagtggcg   3060
ggcgggctcg gtccagggcg agcggggcga cagcctggcc gtggaccgcg gaagggctt   3120 ctggatcgac cacaacccct cggcccccga gccccggcag ggaaacctcc tcacgctgat   3180
ccaggcggcc aaggggctct cccccgagga ggccggcgc tgggcccagc agtggcttgg   3240
cctctcccct tcgccaaagg tcaggcggac gaggagctca ggaccaaagg tcttgagtac   3300
tcaagtgcgt gggagctcgg gtgctccagt ccctgagtct tcaggttccc aggtacctga   3360
ggagtcggac cccttgaca accccgctt ccgggacctc ctcaccccca ggggcgagga   3420
cgaggccccc ttggccccgg cctccgagga ggtgctgcgg cgcatggtgt ctaggcttct   3480 ccgcacccc gaggccgtgg cctacctgaa ggggcgcggt ctggatgccc ggtggtccg   3540 ccgcttctac ctcggcctgg acgacaccgc gcgggccacc ccgcccctgg tctacccggt   3600
gatagggccg gacggctccc ccgttcgccg ccacctctac tacgagatcc ccggcctcac   3660
ccagggcgcc ccgggcaagg ctgggggag ggggaggccc accagctact gggccctccc   3720 cccttcgag ggcccctccc ccgccgcaa gctcttcttg tgcgaggggg cgaaggatgc   3780 ctggccctc tggctccacc tccacgccca gccctgggcc caggacctgg cggtggtgac   3840
ctccacgcac ggctccgccc tccccgaggc ctggaaagac cccctgttct gggccccttg   3900
ggaggaggtc tacctgggcc aggacgccga ctccgccggc gaggagatgg cccggaaggt   3960
ggcggaggtg gcgaggcggc ccgtccgccg cgtccgggtc ccggagggga tggggaagga   4020
ctggacggac tacttcctgg cgggggcac cccgagggc ttgcgcctcc tcctggaggg   4080
agcggaggtc tgggaagaag aagtggctgg aggtgggggc aggatccagc tcccggaccc   4140
cgtggacatc cagcgggcct tcgtgcgggg ccacctctac gtccccgtgc gggtcctgga   4200
```

-continued

```
gaaccggggg gaagaagggg cccgctaccg caccgtggtg gtccgctccg acggggccgt    4260
cctgggctgg ggctacttgc cggccccgcc cggcaccccc ttggaggacc gggtgctggc    4320
cgtggacgac ggcaccatca tccgcaggcc cccgaaggcg gccgccggga cctcgtggaa    4380
cggggaggcc atcaaccgct tcctggaagc ccgggcccgg ggagtgagcg ccatgaccgt    4440
ggccccccgg gacctgcctg ggctcatcgt ccgccacctc cgccaggtga tcctccccag    4500
tgaggacggc tacctcctgg ccgccttagg ggtcatgacc tcctacgtgc agagcgtctt    4560
cgacgccgtg cccctcttcc tcgtggtggg cccgccgggc tcggggaaga cggagttcgc    4620
ccgcctcatg gccgagctgg gggccaacgg cgtggtgatc accggccaga cctccgccgc    4680
caccgccgcc cggatcatcg acgagacggg ggggctggtg gccttcgacg acctggagga    4740
ggtgcgccag cggtcgggga gcgctgaggc ctcccagctg gagcagttcc tcaaggtgtc    4800
ctacaagaag gagaccgcgg tcaagagctg gacggacacc aaggggatgc gggtcctcac    4860
cctcaacttc ttcggggtca aggtgatcac caacacccag gggacggggg acatcctggg    4920
gagccggatg ctggtcatcc gcaccgcccg cctccgggac ctgggcagag gggaggagcg    4980
ccgcccgag gggctctccc ccccaggccc tccaagaact ccgggacaac ctctacatct    5040
gggccatgga gaacgcggcc agcctccacg ccctgtaccg ggagcgcttc gcgggcaagg    5100
gggagcgcct ggacgagatc gccgccccct tgcgtaccat cgcccaccac ctgggggacg    5160
aggagctggc ggcccgcctg gaggacgccc tgcgccggca ggaagggcgc ctggaggaga    5220
ccctttccga tgccgaggtg gtggagaccg ccctcaagga ggccatccgc cagggctacc    5280
ggagccacgt ggccctggtc cacgtgatct tccaggcccg gaagatcttc ggggacgact    5340
ggggccggga gcgcaccgtg gacatccccc ggtggcggga cccaagtgg gtggggcaga    5400
tcgccagcaa ctacggctgg gcggcccag aaaggcccgt gaggcccgg ctttgggaca    5460
agcagttccg catcatgcgc ctggagccca ccttcgtgga gcggtggtc aggggcttcc    5520
tccaggaggg gatccccttg gagcccctga agcaaccct ggcttctgcc tggacacccc    5580
ctgcgccgag tgcgcctacc tgcactggtg cgacctccgg cctgacaagg aaaagtggct    5640
ggagcgctac ggggaggcca agctggccca gaaaaggcgg gagctggagg aggagttttt    5700
ggccctggtg gggccccaag atggccttgg cctccaggct tccgccgagg aggagggaga    5760
ccgaggtaag cacccaagta cccaagtacc caagaccccta aagcctcagg taccggagga    5820
cctcggggac ggaggaccta aaaccccaag ggcgtgaaag actgaggtga gagggatgat    5880
cgtggctgtc accggcttca agggagggt ggggaagacc accacggcgg tccacctggc    5940
ctgcttcctg gccgagcggg gccccaccct gctggtggac ggggacccca accgctccgc    6000
cacggggtgg caccggaggg gaggcctccc ggtgaccgtg gtggacgagc gggtggcggc    6060
ccggtacgcc cgggagcacg cccacgtggt catagacacc caggcccgcc ccacggaaga    6120
ggacctccgg gccctcgcca agggggtgga cctgctggtc ctgcccacgt cccccgacgc    6180
cctggccctg gaggccctcc tggccaccct ggaagccctg cggggggcgg aggcccgctt    6240
ccgggtcctc ctgaccatgg tgcccccgcc cccgagccgg gacggggagg aggcccggc    6300
cctcttgggg gcggagggcg ttcccctctt cacaggctgg gtgaggcggg cggcagcctt    6360
ccccaaggcc gccctcctgg gggtgcctgt ctaccgggtg cccgacccca gggcgaggct    6420
ggcctggggg gactacgcgc gggtggggga agagctcctg aaggaggtgg ggggatgagc    6480
aagttcgcca ggctcctcaa agaggtcaag agagaaggag aggcctccgg ggagcggcct    6540
cgggggaaga gccggcggga ggactacgtg gccatgaagg tctacatcag caaagagctt    6600
```

```
caccggaggc tgaagctgaa ggccctggag gaggagaagg agctttcgga gctggtggaa    6660
gaggccctga ggaagttgct ggtgtgacct cctcccgcct cgtagagcgt gaaaaggagg    6720
taagacgatg gtcacccttta acaaatcgcc cctagaagcc ctctacgcgg gccactcccc    6780
ccaggaggcg ggccgtctct tcgaagcgcc tggtccgcaa gatattgaag gaactccacc    6840
ccatctggag ccaagagttc gtggatgtcg tcccttggtc cgagcacgcc acccgcaagg    6900
ggctcagggc cacggacatc ggcgtggacc tggtgggcta cgggaaggac gacaaggtct    6960
acgccatcca ggtcaagctg tgggataagc ccctctcttg gaaggacctg gggagcttcg    7020
tgggggtggt gaaccacccc gagtacggct tcgaccacgg gctcatcgtg gccccaagag    7080
gcgtgaccca ggaggccgac cgccagctcc agggcctacc catcaccatc ctgagcgaag    7140
aggctctcct agaagacctg gacctggaat ccctcgttcc agaccgcccc gaggaagccc    7200
gcaggcgggg gaagaaggcc ctccgtaagt accagcaaga agccttagag gaggtggcca    7260
aagccttctt agagaagggc ctgccccggg gcaagctcat catgcccccg ggcacgggca    7320
agaccctggt ggccctcaag atcgccgaaa aggtggcggg ccccgggggg aggtcctct    7380 tcctggcgcc ctccatcgcc ctcctggacc agtccctcag ggcctgggcg gcggaggctt    7440
ccttgcccct tgcgcctcttc gccgtggtct cggacacggg cgtgggcaag acctcggagg    7500
acgacctctc cgccctctcc ctcctctcca tccctcctac caccaagcct gaggagctgg    7560
cctccgaggc caagacgagg agtcaggagg ccctcaccgt ggtcttctcc acctaccagt    7620
cggcggaggt cctggagagg gcccagaagg agcacggggct tccccctttt gacctgatga    7680
tcctggacga agcccaccgc acagccacgg tgcgggcggg agaagaaagc ccctttcacca    7740 aggtgcacca cgaccactac gtgaaggccc gccaccgcct ctacatgacg gccacgcccca    7800 ggatctggga ggtggagggg aatggagaga ggggccaagg gaaaaaggcg gggaaaaaga    7860
aggaccctca gaaagagggt tctcctcccc ttttggacct cggtgcctct cctacggagg    7920
actccacggc ccccgaaggg gtggaactcc tggtctactc catggacaac gagggggatct    7980 atggccccac cctctacgag tacaccttca ccccgcgcgt gaaggagggc cacctgagcg    8040
actacaaggt catcgtcttc tccgtggcgg aggaagccca aaaggacctg gcctcctacc    8100
tccagggacc cgaggccctc aaggtggagg aggctctgaa ggccctgggc ctgtggaagg    8160
tcctccaggg ggaggtgcgg gacgaggagg ggaacccgat gggggggcctc gacctgcgga    8220 gagtcatcgc cttccacggc cggggtgaagg agtccaagga gatggaggaa gagttcacga    8280
aggtggccct cgctgcccag caggctggcc tccttcccga ggagctccgg cgggtggagg    8340
tgaagcacat agacgggcag atgtccgcct atgaccggaa cgcctcctg gactggctta    8400 gggagaacgt ccccgagggg gaggtccgcc tcctcaccaa cgccaaggtc ctcaccgagg    8460
ggatcgacgt cccggcccta gatgccgtgg ccttcatgcg tccccgggac agcgtggtgg    8520
acgtgatcca ggccgtgggg cgggccatgc gcaaggcccc gggcaaggag tacgggtacg    8580
tggtcctgcc cgtggtggtg aggggggcagg acgaggagcg ggagatcgag gagagcggct    8640
accgggcggt gtggcaggtg ctctcggcct tgcgctcggt ggacaagtcc ttcgaggccc    8700
gcatgcgggc cgccctggtg cgcctctcgg gtaaggcga gggcgggaa ggtgagagg    8760 cccgagaggg tgtggccgtc atcggggaag gaagcgcctc cccgtgatc gtagatgtcc    8820 ttcaggggaa cctcaacctc caccaggaga tcacccggag cctcgccggc aagctggtca    8880
ggcgcctcgc cctgggggcg aagtacctgg agaactgggc ccaggacgtg gcccgggtgg    8940
cgaaggtgct ggagcagcag gtcagggcga tggcggagcg ggaccccaag gtgaaggaaa    9000
```

-continued

```
aactggggaa actcctcgcc gccctgcagg ccttcaccag cgagagcgtg acggaggacg    9060
aagccatcct catgctggtc cagcacgctc tcaccaagcc catcttcgac gccctcttcg    9120
gggaactcct agaaaagcgg gaggaccccg tttcccgggc cctagacgaa ctcttccagg    9180
agttcagggg gttcctggac cgggaagggg aggccctcaa ggatttctac gaagagatgc    9240
gcctcaaggc cctagggctc acggacgaag ccgaaagggc cgacttccta cggaggctct    9300
actccaactt cttcgcccgg gccttccccc aggtggccga ccaggtgggg atcgcctaca    9360
ccccggtgga gctggtggac ttcctggtga agagcgcaga cgagctggcc aggaagcact    9420
gttggccggg ggctcgatgg ggagaaggtc ttcatcctgg agcccttcgc cggcacaggc    9480
accttcgtca cccgaatcct gcaccgggta gccgaaaggg gcggggccga cgcggtcaag    9540
ggcaagctgg agcggggggga gatctggggcc aacgagatcc ttctcctccc ctactacgtc    9600
ctcagggcca acgtggagaa caccaccctg gccctgaccg ggagtacgt cccccttcaag    9660 ggggcgttct ggcggactcc ttcggctggc ggagctgggg tatagcgaga aaaagtttgg    9720
catcatcccg ctcttcccgg aagaatacgt tgaggccctg aacgagcagc tgaaggcccc    9780
tatccaggtt atcctctcca accccccgtg cgggcttggt tggagaagga gggcgagggg    9840
aagaagaacc ccgtctaccg taaggtgcgg gagcgggtgg agccaaccta tgtacggcgg    9900
gccaaggaac ttcccatcgg ggggacaaaa cccaagggag agaacctgaa ctccctctac    9960
gaccagtaca tccaggcctt gcgggtggcg agcgaccgta tcggggagga gggggtcgtg    10020
gccttcgtca ccaacaacgg gtggctgggg ggcgtagtgc cccggggctt gcgggcctct    10080
ttggcggagg agttcgccga ggtgtacgtc tacgacctga gggggggatgc gagggagaag    10140 gggggaggcac ggaagaagga gggggggcggg gtctttggac agccttcccg cgccggggtc    10200
tgcctcctcc tcctggtgaa gcgtaaggac cacaaaggga tcggcaaggt ccacctctat    10260
cgggtcgggg acgcctctc ccgggaggcc aagctggctc tggtgaagga gcatggctca    10320
gtctctgggt tccctggcaa gaggttccct atgaagagtg ggtggggagg cttaccccccg    10380 ggttctcggg gatgttgtcc ctggacgagg tctttgaggt gcggagttct ggggtgaaga    10440
ccaaccgcga tgcctacgtc ttcaaccccct cccgggcgga gctggagcgg cacatgaggc    10500
ggctcatctc cacctacaac gagcacgtga aaggaaaaa agaggggaaa ctaggggaac    10560
tggaaaagga tgagagcatc atcaagtggg ataggggaact catcaggtac ctagagtccc    10620
tgagggaagc ttcctacgaa gggagcggtc aagtctacga ggccctctac cgccccttcg    10680
tgcctatgta cctctacctc agccgcactt tcaatagcat gatttaccaa atcccccgca    10740
tctggcccac ccccgaggcc gagaacctgg ccatcgccgt ggccggaaag gggagtaacg    10800
cttttagcgc tgtggccacc aggagggtgg ttgacctgca ctttattgag accacccagc    10860
tctaccccct ttaccactac cccgaaaaca gccctctggg gggacaccca agcgcaagc    10920 tcaacctcaa ggaggagttc ttgaggaagc ttggggaggt cctcggccgc cccgttcccc    10980
ccgaggaggc cttcgcttac atctacgccg tggtgagcca cccctctac gccgagcgct    11040 tcgccaagga cctcaagatg gacctccccc gcattcccct ccccaagat cccgaactct    11100 ttgccaggct ggtgaaggcg ggtcaagaac tcattcacct ccacaccgag tacgagaccc    11160 tgccccctg gagcccagtc cccttcgggg tggaagaggg aggcccggag gaccctacga    11220
gcgctaccgg gtggagcgga tgaggctgga caaggagagg agggttctcc agtacaacga    11280
ctgggtccgg gtggagggca tccccgagga ggccttcgc tggcgcccg gggggtactc    11340 cccccttggag tggattggcc gcttctggaa ggtggaggag aagtgcccca agggcagggg    11400
```

-continued

```
ggaggccatc gtctgggacc ccaacctctt cctcaaggag aagggggaac cccgttacct    11460
cctggacctc atcgggcggg cggtccaggt ggccgtgcag acggttggga tccacgagga    11520
gctgagagaa gacgtggaag ctctgctggg ttgaggtggt gctggcccgc cgttctccct    11580
actcctttag ggcctacccc tacgatccaa gcacggccct gggggggcgct caggtgggca    11640
```

```
ggaggccatc gtctgggacc ccaacctctt cctcaaggag aagggggaac cccgttacct    11460
cctggacctc atcgggcggg cggtccaggt ggccgtgcag acggttggga tccacgagga    11520
gctgagagaa gacgtggaag ctctgctggg ttgaggtggt gctggcccgc cgttctccct    11580
actcctttag ggcctacccc tacgatccaa gcacggccct ggggggcgct caggtgggca    11640
tcccacgtcc aaggccccga cttgggcacc ccatgctgcg aacttacagc ccaagggcct    11700
gaaacattcc cccctgctca cgggggaaag ttcgtgaagg aaagagcaaa gcctttttta    11760
tcgcatccgg agagatggcg gggtggaact tttccccgag gactccccca tagggacatg    11820
taaacggcaa gctatcagtg tagacttttt tcaaaagag ccatactcgt gttttcccgt    11880
tcagaacggc atttttgcta aggaggtggt ttacaaatgg gtgttaatgc gctacatcct    11940
ccggtagtag gagcatgc                                                  11958
```

<210> SEQ ID NO 9
<211> LENGTH: 10
<212> TYPE: DNA
<213> ORGANISM: Thermus sp.

<400> SEQUENCE: 9

```
ggcttttctt                                                                10
```

<210> SEQ ID NO 10
<211> LENGTH: 10
<212> TYPE: DNA
<213> ORGANISM: Thermus sp.

<400> SEQUENCE: 10

```
aacttttccc                                                                10
```

<210> SEQ ID NO 11
<211> LENGTH: 10
<212> TYPE: DNA
<213> ORGANISM: Thermus sp.

<400> SEQUENCE: 11

```
gacttttttc                                                                10
```

<210> SEQ ID NO 12
<211> LENGTH: 7
<212> TYPE: DNA
<213> ORGANISM: Thermus sp.

<400> SEQUENCE: 12

```
aactttg                                                                    7
```

<210> SEQ ID NO 13
<211> LENGTH: 7
<212> TYPE: DNA
<213> ORGANISM: Thermus sp.

<400> SEQUENCE: 13

```
agttttg                                                                    7
```

<210> SEQ ID NO 14
<211> LENGTH: 7
<212> TYPE: DNA
<213> ORGANISM: Thermus sp.

<400> SEQUENCE: 14

```
gattttg                                                                    7
```

```
<210> SEQ ID NO 15
<211> LENGTH: 7
<212> TYPE: DNA
<213> ORGANISM: Thermus sp.

<400> SEQUENCE: 15 aactttg                                                              7

<210> SEQ ID NO 16
<211> LENGTH: 25
<212> TYPE: DNA
<213> ORGANISM: Thermus sp.

<400> SEQUENCE: 16
ggttccataa ggcgggtcaa tatag                                          25

<210> SEQ ID NO 17
<211> LENGTH: 25
<212> TYPE: DNA
<213> ORGANISM: Thermus sp.

<400> SEQUENCE: 17
ctatattgac ccgccttatg gaacc                                          25

<210> SEQ ID NO 18
<211> LENGTH: 27
<212> TYPE: DNA
<213> ORGANISM: Thermus sp.

<400> SEQUENCE: 18
gtggggtggg ctgatcaaga atctcct                                        27

<210> SEQ ID NO 19
<211> LENGTH: 27
<212> TYPE: DNA
<213> ORGANISM: Thermus sp.

<400> SEQUENCE: 19
aggagattct tgatcagccc accccac                                        27

<210> SEQ ID NO 20
<211> LENGTH: 26
<212> TYPE: DNA
<213> ORGANISM: Thermus sp.

<400> SEQUENCE: 20
tcacccacaa ccctcacgca ctccaa                                         26

<210> SEQ ID NO 21
<211> LENGTH: 26
<212> TYPE: DNA
<213> ORGANISM: Thermus sp.

<400> SEQUENCE: 21
ttggagtgcg tgagggttgt gggtga                                         26

<210> SEQ ID NO 22
<211> LENGTH: 26
<212> TYPE: DNA
<213> ORGANISM: Thermus sp.

<400> SEQUENCE: 22
agatgtagtc gtccagggtg agcctg                                         26
```

-continued

```
<210> SEQ ID NO 23
<211> LENGTH: 26
<212> TYPE: DNA
<213> ORGANISM: Thermus sp.

<400> SEQUENCE: 23
caggctcacc ctggacgact acatct                                            26

<210> SEQ ID NO 24
<211> LENGTH: 25
<212> TYPE: DNA
<213> ORGANISM: Thermus sp.

<400> SEQUENCE: 24
ttggtatgta aagcccttcg cgagg                                             25

<210> SEQ ID NO 25
<211> LENGTH: 25
<212> TYPE: DNA
<213> ORGANISM: Thermus sp.

<400> SEQUENCE: 25
cctcgcgaag ggctttacat accaa                                             25

<210> SEQ ID NO 26
<211> LENGTH: 25
<212> TYPE: DNA
<213> ORGANISM: Thermus sp.

<400> SEQUENCE: 26
tagtggcatc ggtgttgtcg tgggt                                             25

<210> SEQ ID NO 27
<211> LENGTH: 25
<212> TYPE: DNA
<213> ORGANISM: Thermus sp.

<400> SEQUENCE: 27
acccacgaca acaccgatgc cacta                                             25

<210> SEQ ID NO 28
<211> LENGTH: 14
<212> TYPE: DNA
<213> ORGANISM: Thermus sp.

<400> SEQUENCE: 28
ctagtctaga ctag                                                         14

<210> SEQ ID NO 29
<211> LENGTH: 9
<212> TYPE: DNA
<213> ORGANISM: Thermus sp.

<400> SEQUENCE: 29 ttatcaccc                                                                9

<210> SEQ ID NO 30
<211> LENGTH: 9
<212> TYPE: DNA
<213> ORGANISM: Thermus sp.

<400> SEQUENCE: 30 ttatccgag                                                                9
```